(12) United States Patent
Losordo et al.

(10) Patent No.: US 9,962,164 B2
(45) Date of Patent: *May 8, 2018

(54) WING BIFURCATION RECONSTRUCTION DEVICE

(71) Applicant: Covidien LP, Mansfield, MA (US)

(72) Inventors: Michael Losordo, San Juan Capistrano, CA (US); Jianlu Ma, Irvine, CA (US)

(73) Assignee: Covidien LP, Mansfield, MA (US)

( * ) Notice: Subject to any disclaimer, the term of this patent is extended or adjusted under 35 U.S.C. 154(b) by 341 days.

This patent is subject to a terminal disclaimer.

(21) Appl. No.: 14/919,268

(22) Filed: Oct. 21, 2015

(65) Prior Publication Data
US 2016/0038153 A1 Feb. 11, 2016

Related U.S. Application Data

(63) Continuation of application No. 13/664,648, filed on Oct. 31, 2012, now Pat. No. 9,186,267.

(51) Int. Cl.
*A61F 2/954* (2013.01)
*A61F 2/856* (2013.01)
(Continued)

(52) U.S. Cl.
CPC .... *A61B 17/12172* (2013.01); *A61B 17/1214* (2013.01); *A61B 17/12036* (2013.01);
(Continued)

(58) Field of Classification Search
CPC .... A61F 2/82; A61F 2/844; A61F 2/86; A61F 2/90; A61F 2/91; A61F 2002/821;
(Continued)

(56) References Cited

U.S. PATENT DOCUMENTS

| 4,921,484 A | 5/1990 | Hillstead |
| 5,122,136 A | 6/1992 | Guglielmi et al. |

(Continued)

FOREIGN PATENT DOCUMENTS

| CN | 1556689 A | 12/2004 |
| CN | 101415449 A | 4/2009 |

(Continued)

OTHER PUBLICATIONS

U.S. Appl. No. 13/312,887, filed Dec. 6, 2011, 2012/0143317.
(Continued)

*Primary Examiner* — Todd J Scherbel
(74) *Attorney, Agent, or Firm* — Fortem IP LLP; Matthew Lincicum

(57) ABSTRACT

An intraluminal device may be used at a bifurcation to anchor in an afferent vessel, allow perfusion to efferent vessels, and act as scaffolding to inhibit herniation of objects out of a neck of a bifurcation aneurysm. An intraluminal device may include a first side; a second side opposite the first side across a longitudinal axis of the intraluminal device; a proximal section configured to anchor in an afferent vessel; a distal section comprising a first wing and a second wing wherein, in an expanded state, the first wing extends from the first side to the second side and the second wing extends from the second side, through an opening of the first wing, and to the first side.

20 Claims, 28 Drawing Sheets

(51) Int. Cl.
  *A61B 17/12* (2006.01)
  *A61F 2/82* (2013.01)
  *A61F 2/91* (2013.01)
  *A61F 2/844* (2013.01)
  *A61F 2/915* (2013.01)
  *A61F 2/852* (2013.01)

(52) U.S. Cl.
  CPC .......... *A61B 17/12118* (2013.01); *A61F 2/82* (2013.01); *A61F 2/844* (2013.01); *A61F 2/856* (2013.01); *A61F 2/91* (2013.01); *A61F 2/915* (2013.01); *A61F 2/954* (2013.01); *A61B 2017/1205* (2013.01); *A61B 2017/12081* (2013.01); *A61F 2/852* (2013.01); *A61F 2002/823* (2013.01); *A61F 2002/91541* (2013.01); *A61F 2220/005* (2013.01); *A61F 2220/0058* (2013.01); *A61F 2230/0052* (2013.01); *A61F 2230/0095* (2013.01)

(58) Field of Classification Search
  CPC ......... A61F 2002/823; A61B 17/12022; A61B 17/12113; A61B 17/12118; A61B 17/12168; A61B 17/12172
  See application file for complete search history.

(56) References Cited

U.S. PATENT DOCUMENTS

| | | |
|---|---|---|
| 5,624,461 A | 4/1997 | Mariant |
| 5,645,558 A | 7/1997 | Horton |
| 5,690,671 A | 11/1997 | McGurk et al. |
| 5,725,552 A | 3/1998 | Kotula et al. |
| 5,728,906 A | 3/1998 | Eguchi et al. |
| 5,733,294 A | 3/1998 | Forber et al. |
| 5,879,366 A | 3/1999 | Shaw et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,951,599 A | 9/1999 | McCrory |
| 5,957,948 A | 9/1999 | Mariant |
| 6,024,756 A | 2/2000 | Huebsch et al. |
| 6,036,720 A | 3/2000 | Abrams et al. |
| 6,063,070 A | 5/2000 | Eder |
| 6,063,104 A | 5/2000 | Villar et al. |
| 6,086,577 A | 7/2000 | Ken et al. |
| 6,096,073 A | 8/2000 | Webster et al. |
| 6,168,615 B1 | 1/2001 | Ken et al. |
| 6,168,622 B1 | 1/2001 | Mazzocchi |
| 6,221,086 B1 | 4/2001 | Forber |
| 6,261,305 B1 | 7/2001 | Marotta et al. |
| 6,306,141 B1 | 10/2001 | Jervis |
| 6,309,367 B1 | 10/2001 | Boock |
| 6,322,576 B1 | 11/2001 | Wallace et al. |
| 6,325,820 B1 | 12/2001 | Khosravi et al. |
| 6,331,184 B1 | 12/2001 | Abrams |
| 6,344,048 B1 | 2/2002 | Chin et al. |
| 6,346,117 B1 | 2/2002 | Greenhalgh |
| 6,350,270 B1 | 2/2002 | Roue |
| 6,375,668 B1 | 4/2002 | Gifford et al. |
| 6,428,558 B1 | 8/2002 | Jones et al. |
| 6,454,780 B1 | 9/2002 | Wallace |
| 6,506,204 B2 | 1/2003 | Mazzocchi |
| 6,517,558 B2 | 2/2003 | Gittings et al. |
| 6,551,303 B1 | 4/2003 | Van Tassel et al. |
| 6,582,463 B1 | 6/2003 | Mowry et al. |
| 6,585,748 B1 | 7/2003 | Jeffree |
| 6,585,756 B1 | 7/2003 | Strecker |
| 6,589,256 B2 | 7/2003 | Forber |
| 6,589,265 B1 | 7/2003 | Palmer et al. |
| 6,605,102 B1 | 8/2003 | Mazzocchi et al. |
| 6,605,111 B2 | 8/2003 | Bose et al. |
| 6,635,068 B1 | 10/2003 | Dubrul et al. |
| 6,635,069 B1 | 10/2003 | Teoh et al. |
| 6,666,883 B1 | 12/2003 | Seguin et al. |
| 6,669,717 B2 | 12/2003 | Marotta et al. |
| 6,669,721 B1 | 12/2003 | Bose et al. |
| 6,676,696 B1 | 1/2004 | Marotta et al. |
| 6,695,876 B1 | 2/2004 | Marotta et al. |
| 6,712,835 B2 | 3/2004 | Mazzocchi et al. |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,797,083 B2 | 9/2004 | Peterson |
| 6,802,851 B2 | 10/2004 | Jones et al. |
| 6,860,893 B2 | 3/2005 | Wallace et al. |
| 6,949,103 B2 | 9/2005 | Mazzocchi et al. |
| 6,953,472 B2 | 10/2005 | Palmer et al. |
| 6,989,019 B2 | 1/2006 | Mazzocchi et al. |
| 6,994,717 B2 | 2/2006 | Konya et al. |
| 7,029,487 B2 | 4/2006 | Greene, Jr. et al. |
| 7,033,375 B2 | 4/2006 | Mazzocchi et al. |
| 7,048,752 B2 | 5/2006 | Mazzocchi et al. |
| 7,128,736 B1 | 10/2006 | Abrams et al. |
| 7,195,636 B2 | 3/2007 | Avellanet et al. |
| 7,229,461 B2 | 6/2007 | Chin et al. |
| 7,232,461 B2 | 6/2007 | Ramer |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,582,111 B2 | 9/2009 | Krolik et al. |
| 7,621,928 B2 | 11/2009 | Thramann et al. |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,744,652 B2 | 6/2010 | Morsi |
| 7,763,011 B2 | 7/2010 | Ortiz et al. |
| 7,763,065 B2 | 7/2010 | Schmid et al. |
| 7,828,815 B2 | 11/2010 | Mazzocchi et al. |
| 7,828,816 B2 | 11/2010 | Mazzocchi et al. |
| 7,833,259 B2 | 11/2010 | Boatman |
| 7,862,604 B1 | 1/2011 | Marcade et al. |
| 7,887,576 B2 | 2/2011 | Bahler et al. |
| 7,914,567 B2 | 3/2011 | Pavcnik et al. |
| 7,922,732 B2 | 4/2011 | Mazzocchi et al. |
| 7,951,192 B2 | 5/2011 | Yadin et al. |
| 8,388,650 B2 | 3/2013 | Gerberding et al. |
| 8,915,950 B2 | 12/2014 | Cam et al. |
| 9,186,267 B2 | 11/2015 | Losordo et al. |
| 2001/0007946 A1 | 7/2001 | Lenker et al. |
| 2003/0028209 A1 | 2/2003 | Teoh et al. |
| 2003/0171739 A1 | 9/2003 | Murphy et al. |
| 2003/0195553 A1 | 10/2003 | Wallace et al. |
| 2004/0111112 A1 | 6/2004 | Hoffmann |
| 2004/0172056 A1 | 9/2004 | Guterman et al. |
| 2004/0186562 A1 | 9/2004 | Cox |
| 2004/0193206 A1 | 9/2004 | Gerberding et al. |
| 2004/0249408 A1 | 12/2004 | Murphy et al. |
| 2005/0033409 A1 | 2/2005 | Burke et al. |
| 2005/0096728 A1 | 5/2005 | Ramer |
| 2006/0052816 A1 | 3/2006 | Bates et al. |
| 2006/0058864 A1 | 3/2006 | Schaeffer et al. |
| 2006/0064151 A1 | 3/2006 | Guterman et al. |
| 2006/0190070 A1 | 8/2006 | Dieck et al. |
| 2006/0264905 A1 | 11/2006 | Eskridge et al. |
| 2006/0264907 A1 | 11/2006 | Eskridge et al. |
| 2007/0016243 A1 | 1/2007 | Ramaiah et al. |
| 2007/0088387 A1 | 4/2007 | Eskridge et al. |
| 2007/0106311 A1 | 5/2007 | Wallace et al. |
| 2007/0173928 A1 | 7/2007 | Morsi |

(56) References Cited

U.S. PATENT DOCUMENTS

| | | |
|---|---|---|
| 2007/0191884 A1 | 8/2007 | Eskridge et al. |
| 2007/0198075 A1 | 8/2007 | Levy |
| 2007/0203567 A1 | 8/2007 | Levy |
| 2007/0225794 A1 | 9/2007 | Thramann et al. |
| 2007/0225798 A1 | 9/2007 | Gregorich |
| 2007/0265656 A1 | 11/2007 | Amplatz et al. |
| 2007/0270902 A1 | 11/2007 | Slazas et al. |
| 2008/0058856 A1 | 3/2008 | Ramaiah et al. |
| 2008/0109063 A1 | 5/2008 | Hancock et al. |
| 2008/0114436 A1 | 5/2008 | Dieck et al. |
| 2008/0114439 A1 | 5/2008 | Ramaiah et al. |
| 2008/0125806 A1 | 5/2008 | Mazzocchi et al. |
| 2008/0221600 A1 | 9/2008 | Dieck et al. |
| 2009/0043371 A1 | 2/2009 | Fearnot |
| 2009/0069806 A1 | 3/2009 | De La Mora Levy et al. |
| 2009/0118811 A1 | 5/2009 | Moloney |
| 2009/0143851 A1 | 6/2009 | Paul, Jr. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosqueta et al. |
| 2010/0004726 A1 | 1/2010 | Hancock et al. |
| 2010/0004761 A1 | 1/2010 | Flanders et al. |
| 2010/0023105 A1 | 1/2010 | Levy et al. |
| 2010/0069948 A1 | 3/2010 | Veznedaroglu et al. |
| 2010/0094335 A1 | 4/2010 | Gerberding et al. |
| 2011/0022149 A1 | 1/2011 | Cox et al. |
| 2011/0046719 A1 | 2/2011 | Frid |
| 2011/0160757 A1 | 6/2011 | Ferrera et al. |
| 2011/0184452 A1 | 7/2011 | Huynh et al. |
| 2011/0184453 A1 | 7/2011 | Levy et al. |
| 2011/0245862 A1 | 10/2011 | Dieck et al. |
| 2012/0143237 A1 | 6/2012 | Cam et al. |
| 2012/0143317 A1 | 6/2012 | Cam et al. |
| 2012/0296362 A1 | 11/2012 | Cam et al. |
| 2012/0323160 A1 | 12/2012 | Babkes |
| 2013/0204290 A1 | 8/2013 | Clarke et al. |
| 2013/0304109 A1 | 11/2013 | Abrams et al. |
| 2014/0058420 A1 | 2/2014 | Hannes et al. |
| 2014/0121752 A1 | 5/2014 | Losordo et al. |
| 2015/0164665 A1 | 6/2015 | Cam et al. |

FOREIGN PATENT DOCUMENTS

| | | |
|---|---|---|
| CN | 102137626 A | 7/2011 |
| CN | 102361602 A | 2/2012 |
| CN | 102740799 A | 10/2012 |
| CN | 102762156 A | 10/2012 |
| DE | 102008028308 A1 | 4/2009 |
| EP | 1527753 A2 | 5/2005 |
| WO | WO-97/26939 A1 | 7/1997 |
| WO | WO-98/50102 A1 | 11/1998 |
| WO | WO-99/05977 A1 | 2/1999 |
| WO | WO-2001/093782 A1 | 12/2001 |
| WO | WO-2002/000139 A1 | 1/2002 |
| WO | WO-2005/117718 A1 | 12/2005 |
| WO | WO-2006/034166 A2 | 3/2006 |
| WO | WO-2006/119422 A2 | 11/2006 |
| WO | WO-2007/047851 A2 | 4/2007 |
| WO | WO-2008/022327 A2 | 2/2008 |
| WO | WO-2008151204 A1 | 12/2008 |
| WO | WO-2009/076515 A1 | 6/2009 |
| WO | WO-2009/135166 A2 | 11/2009 |
| WO | WO-2010/028314 A1 | 3/2010 |
| WO | WO-2010/030991 A1 | 3/2010 |
| WO | WO-2011/029063 A2 | 3/2011 |
| WO | WO-2012/078678 A1 | 6/2012 |
| WO | WO-2012/154782 A1 | 11/2012 |

OTHER PUBLICATIONS

U.S. Appl. No. 13/664,648, filed Oct. 31, 2012, 2014/0121752.
U.S. Appl. No. 13/312,889, filed Dec. 6, 2011, U.S. Pat. No. 8,915,950.
U.S. Appl. No. 13/473,840, filed May 17, 2012, 2012/0296362.
U.S. Appl. No. 13/578,554, filed Dec. 22, 2014, 2015/0164665.
Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

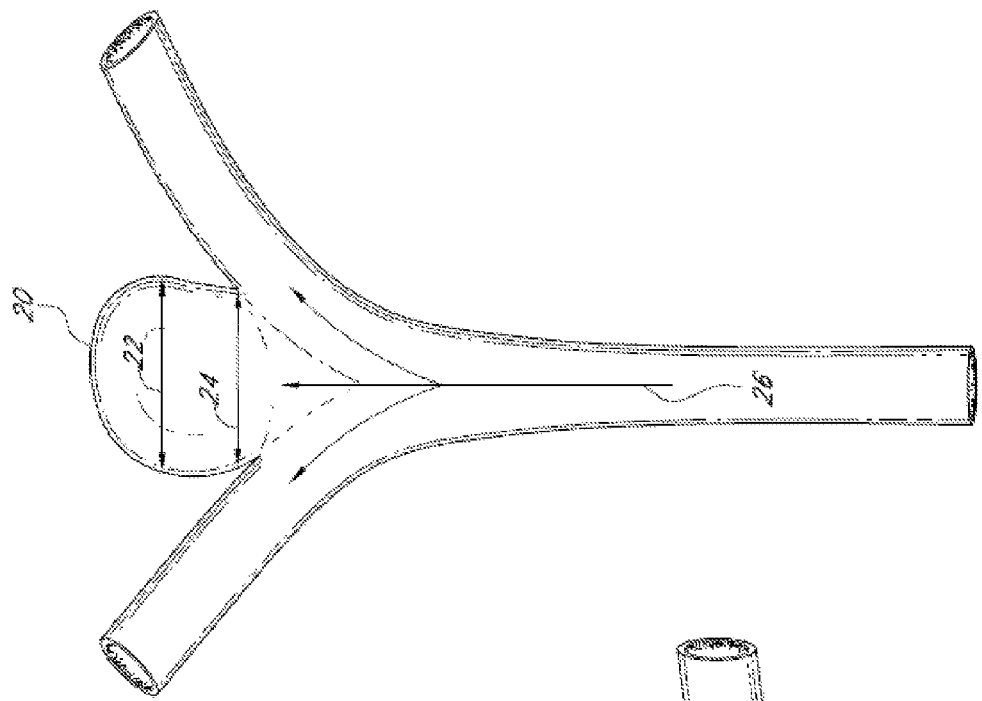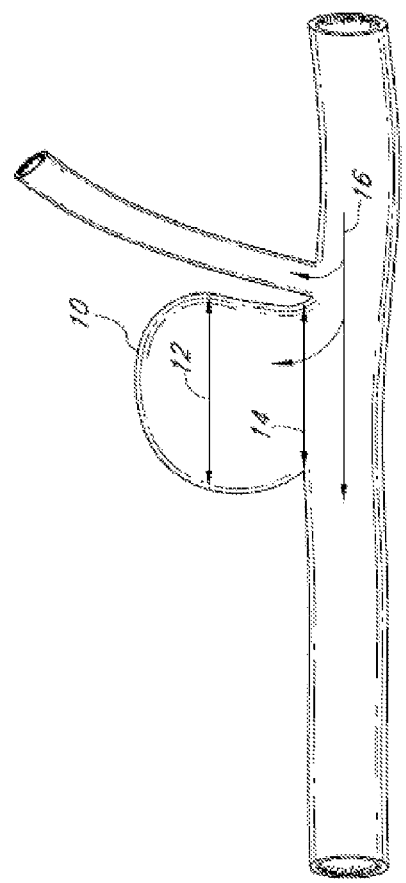

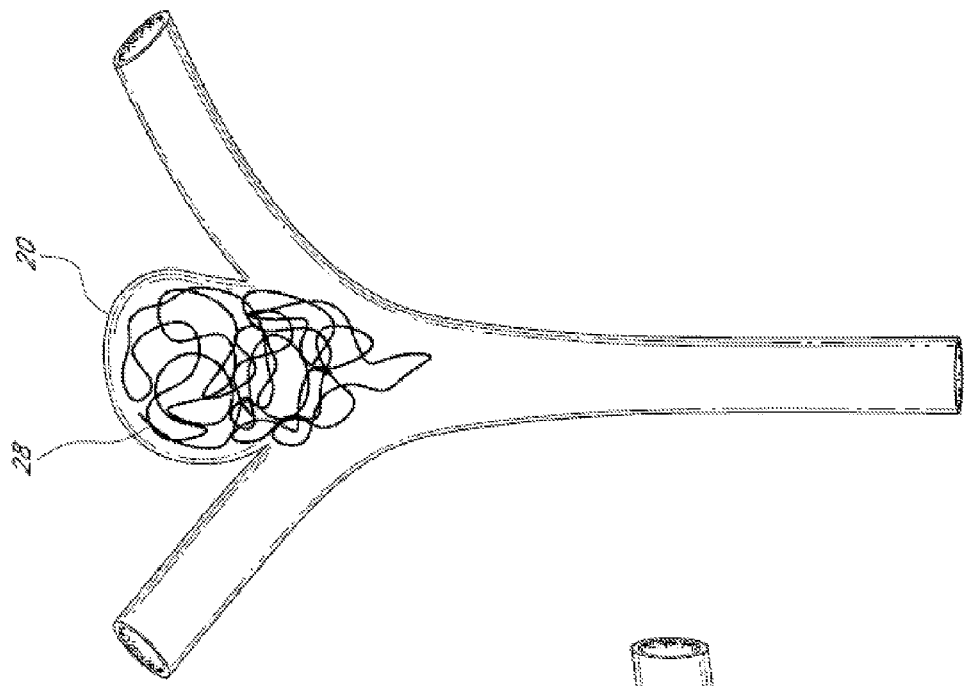
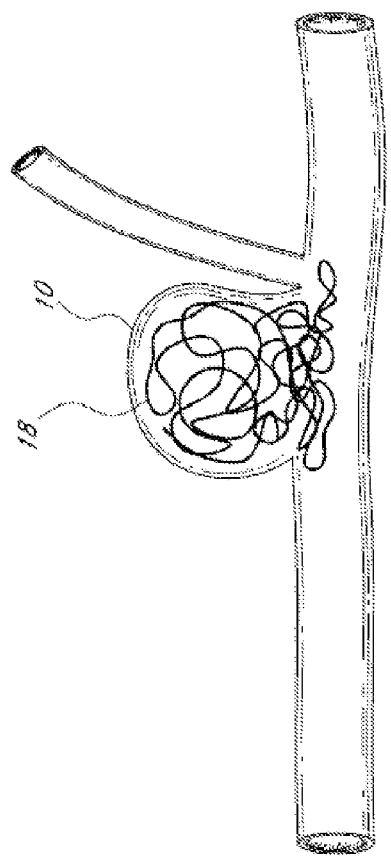
FIG. 3B
FIG. 3A

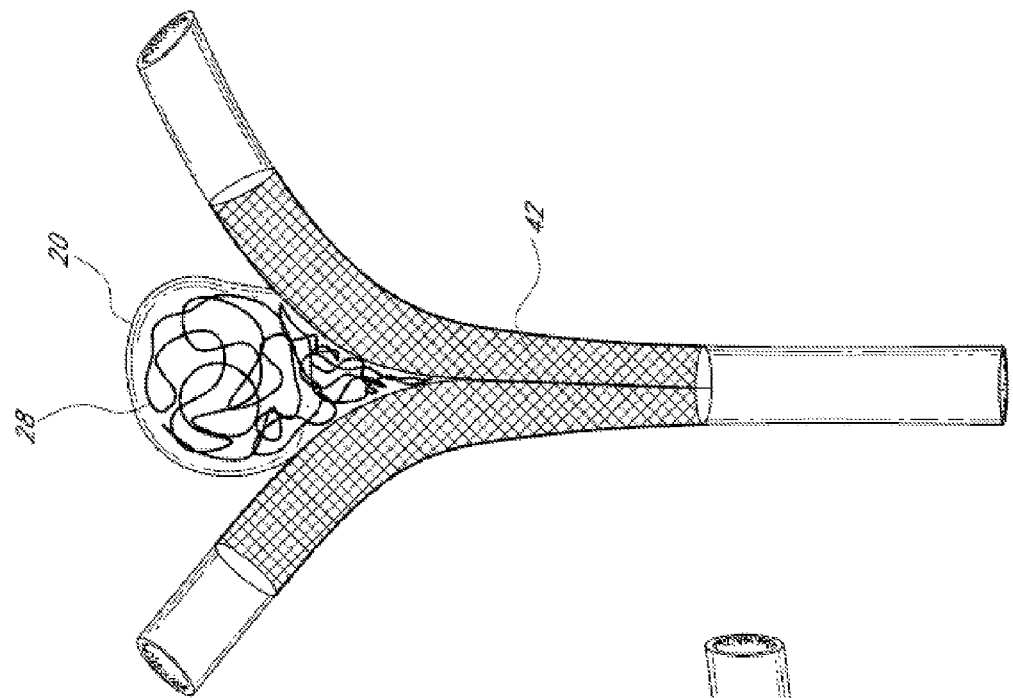
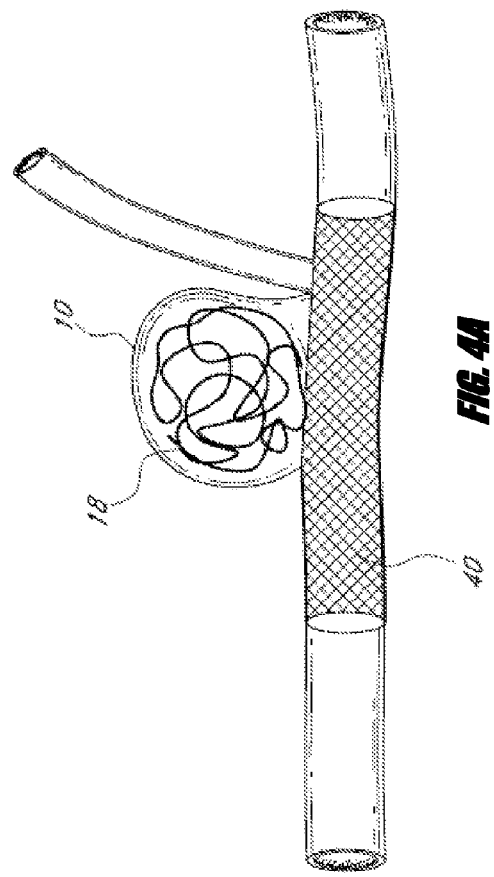
FIG. 4B
FIG. 4A

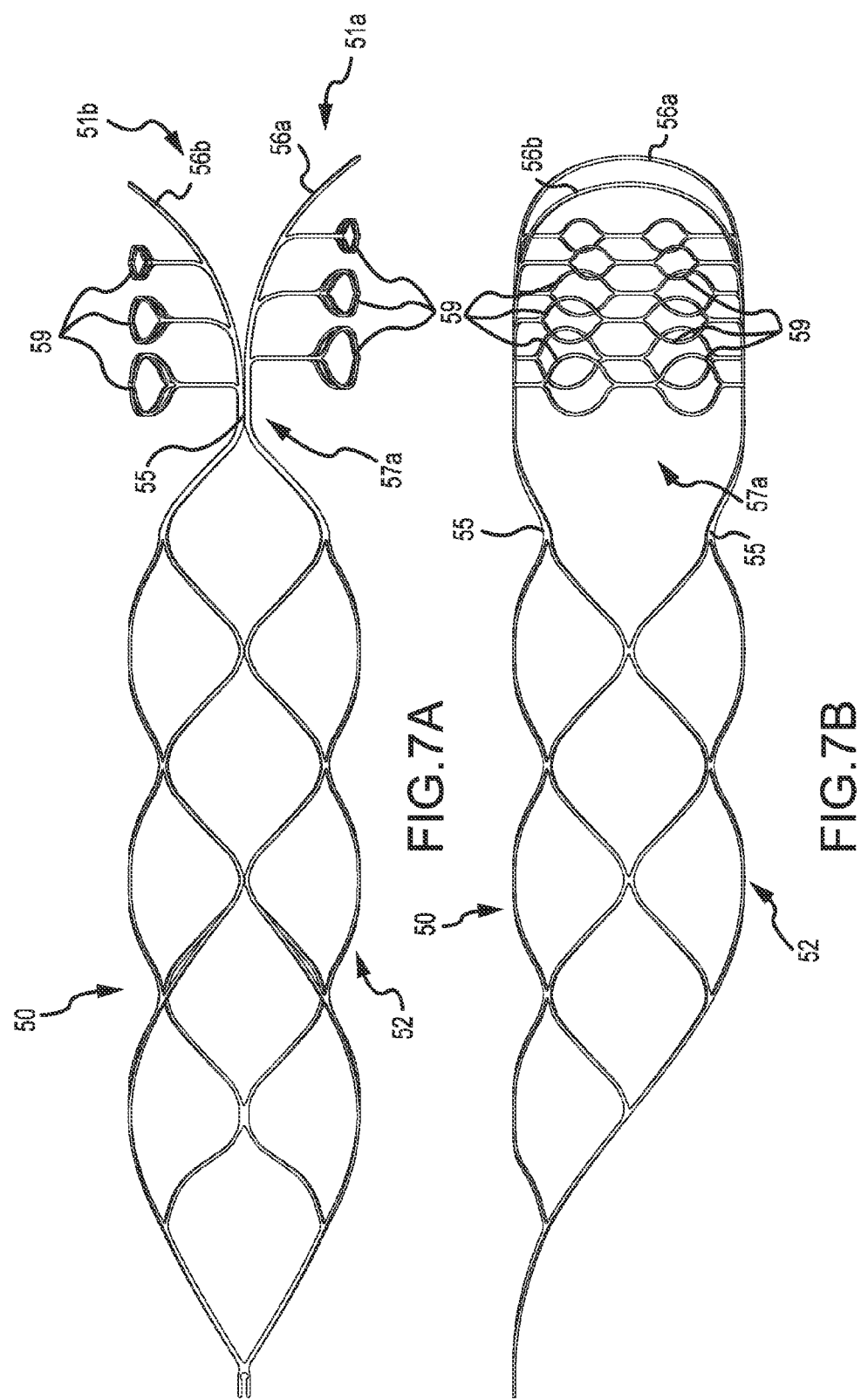

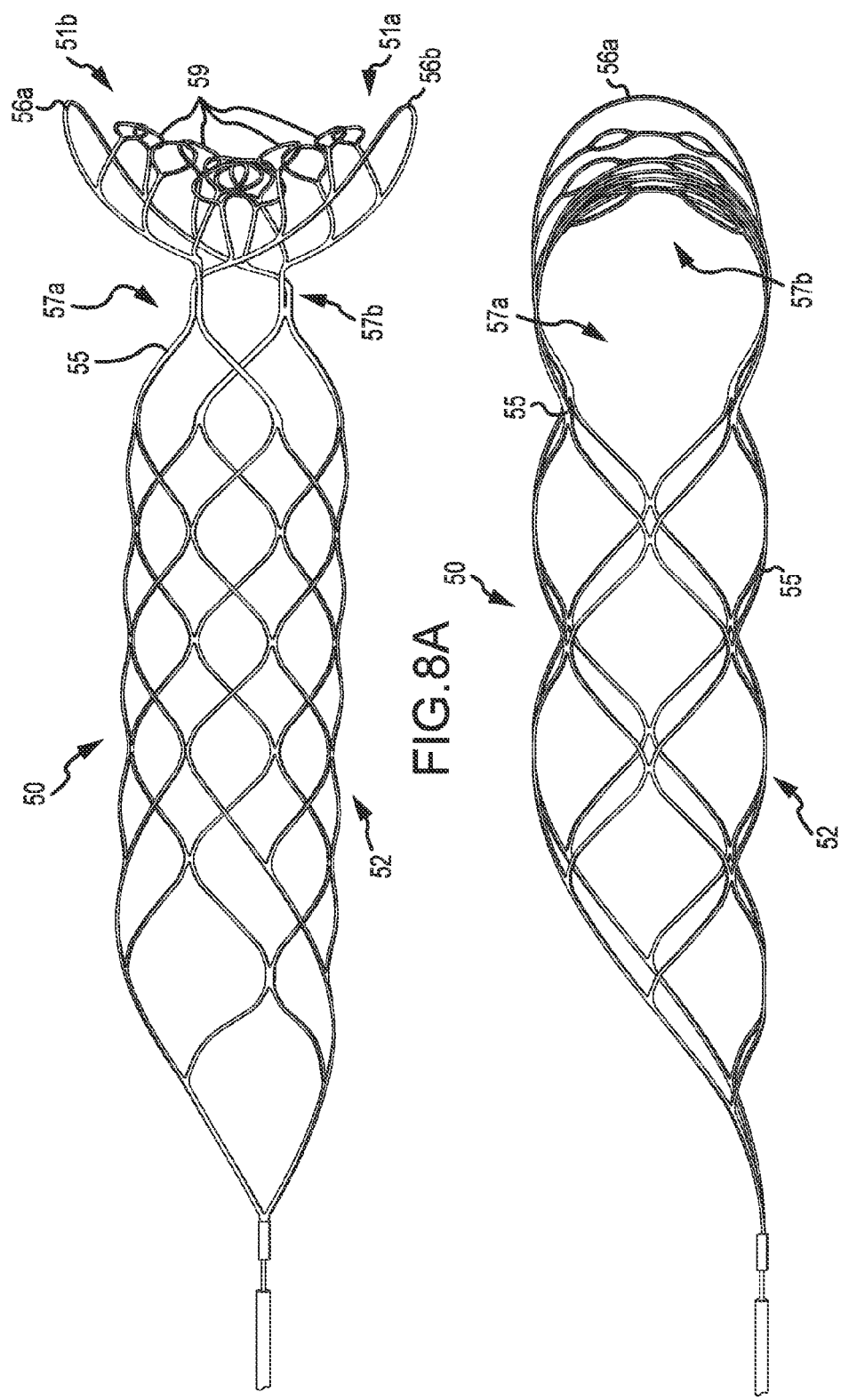

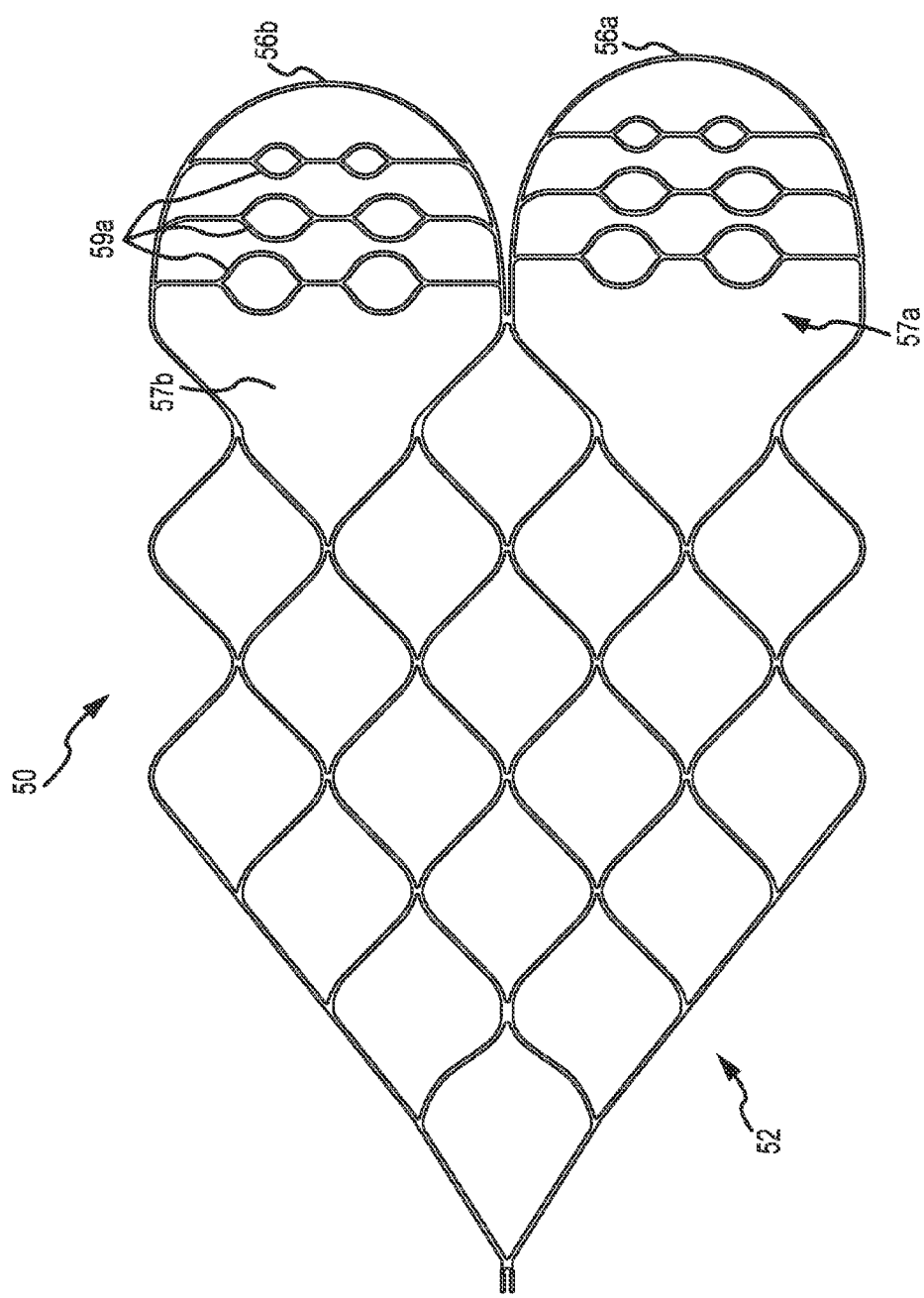

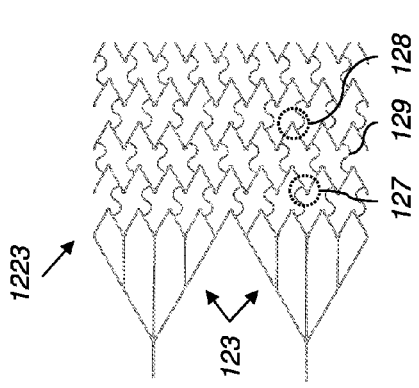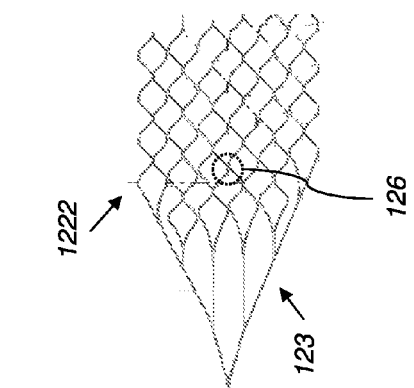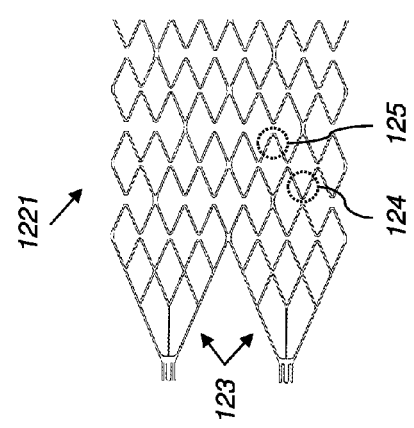
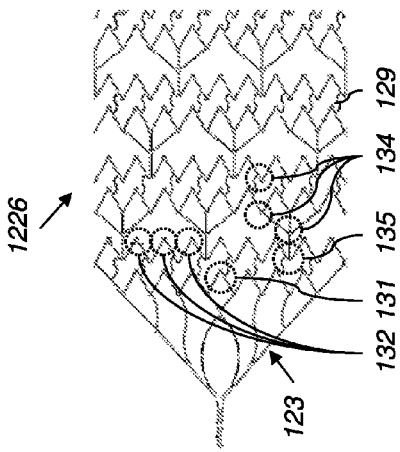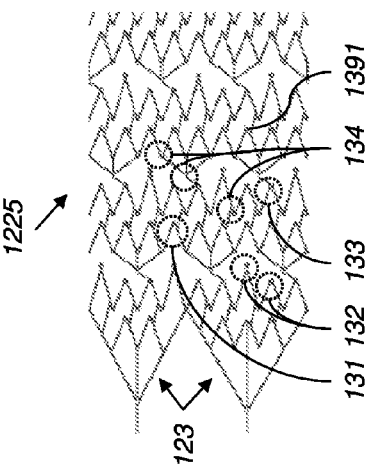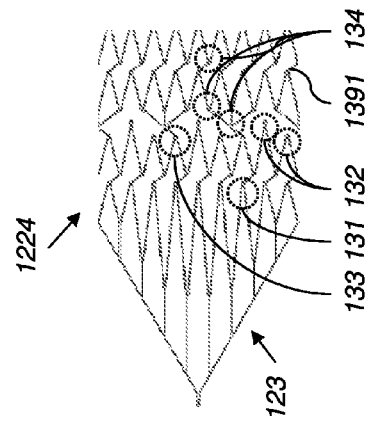

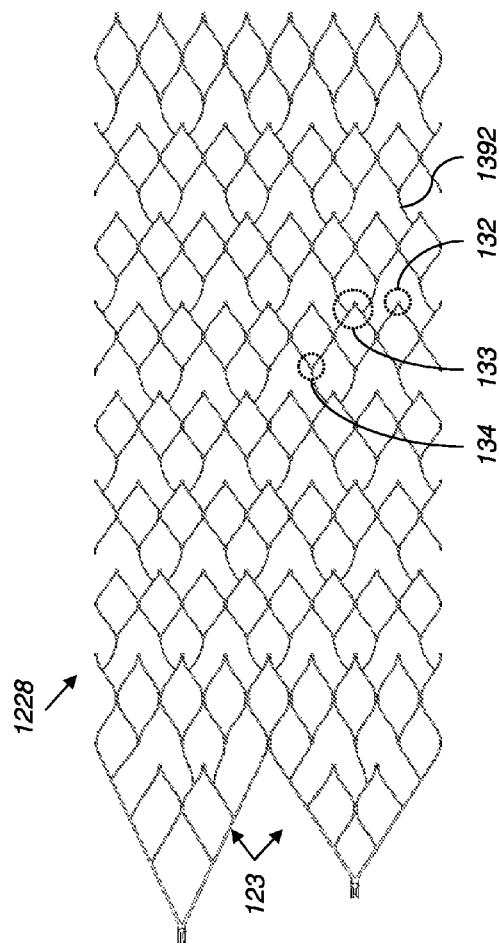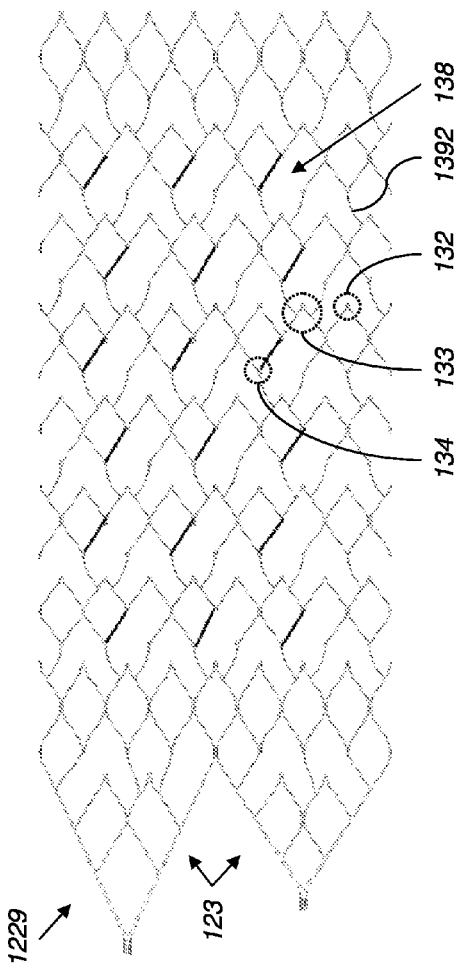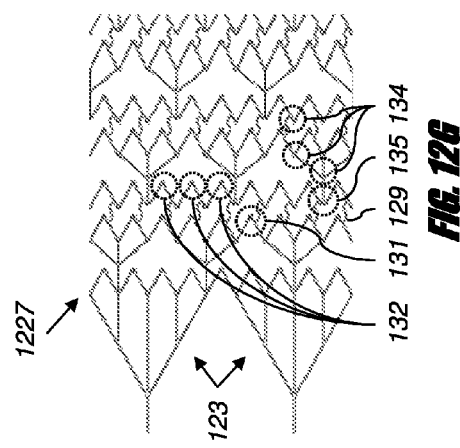

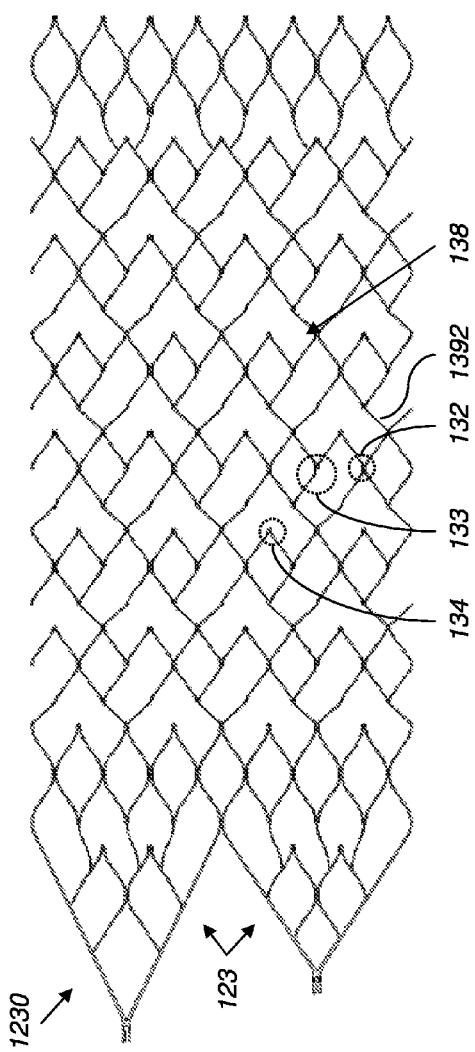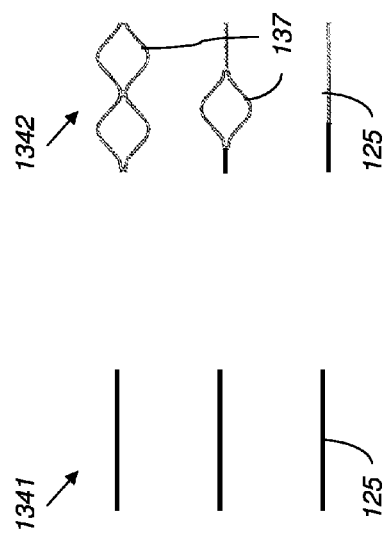

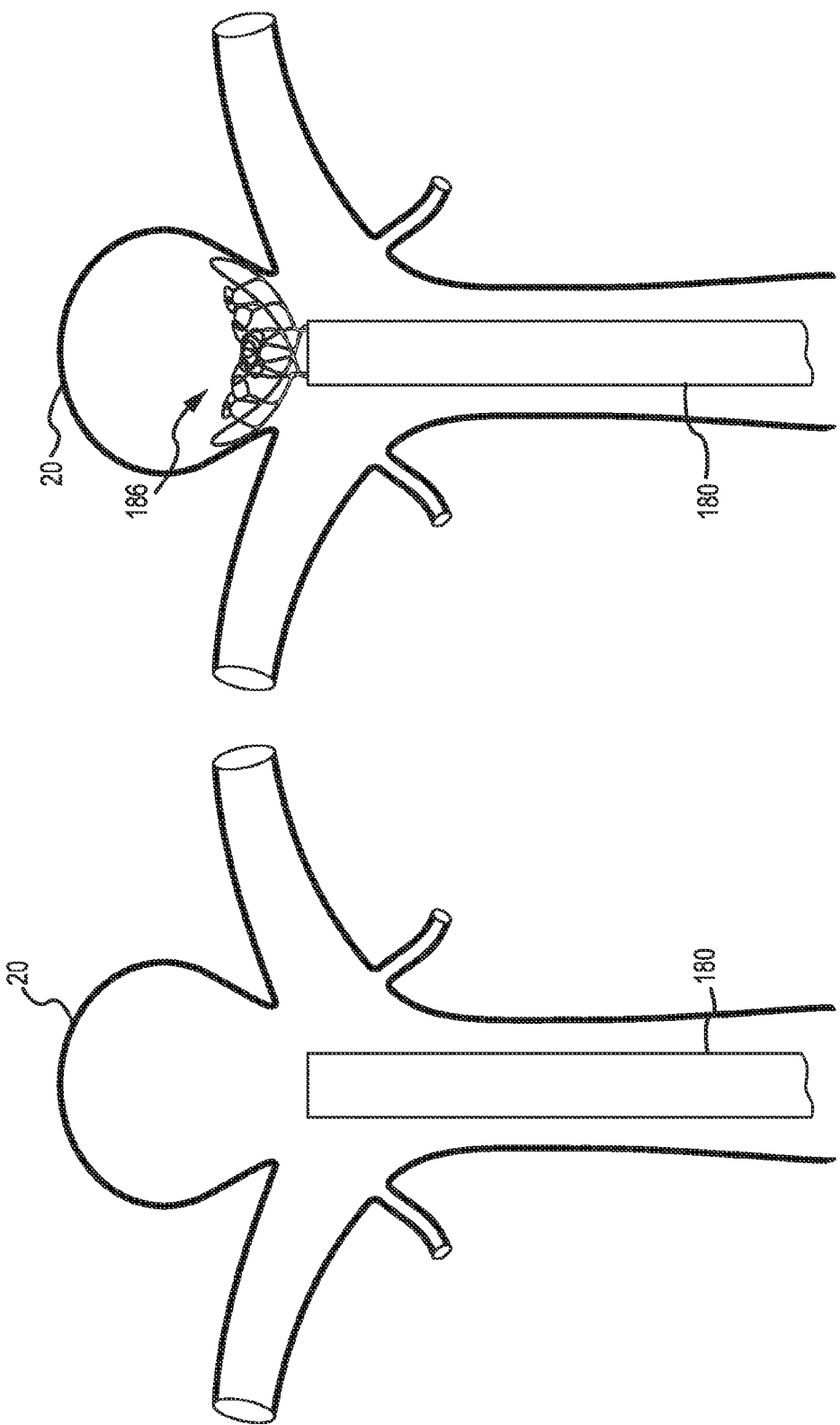

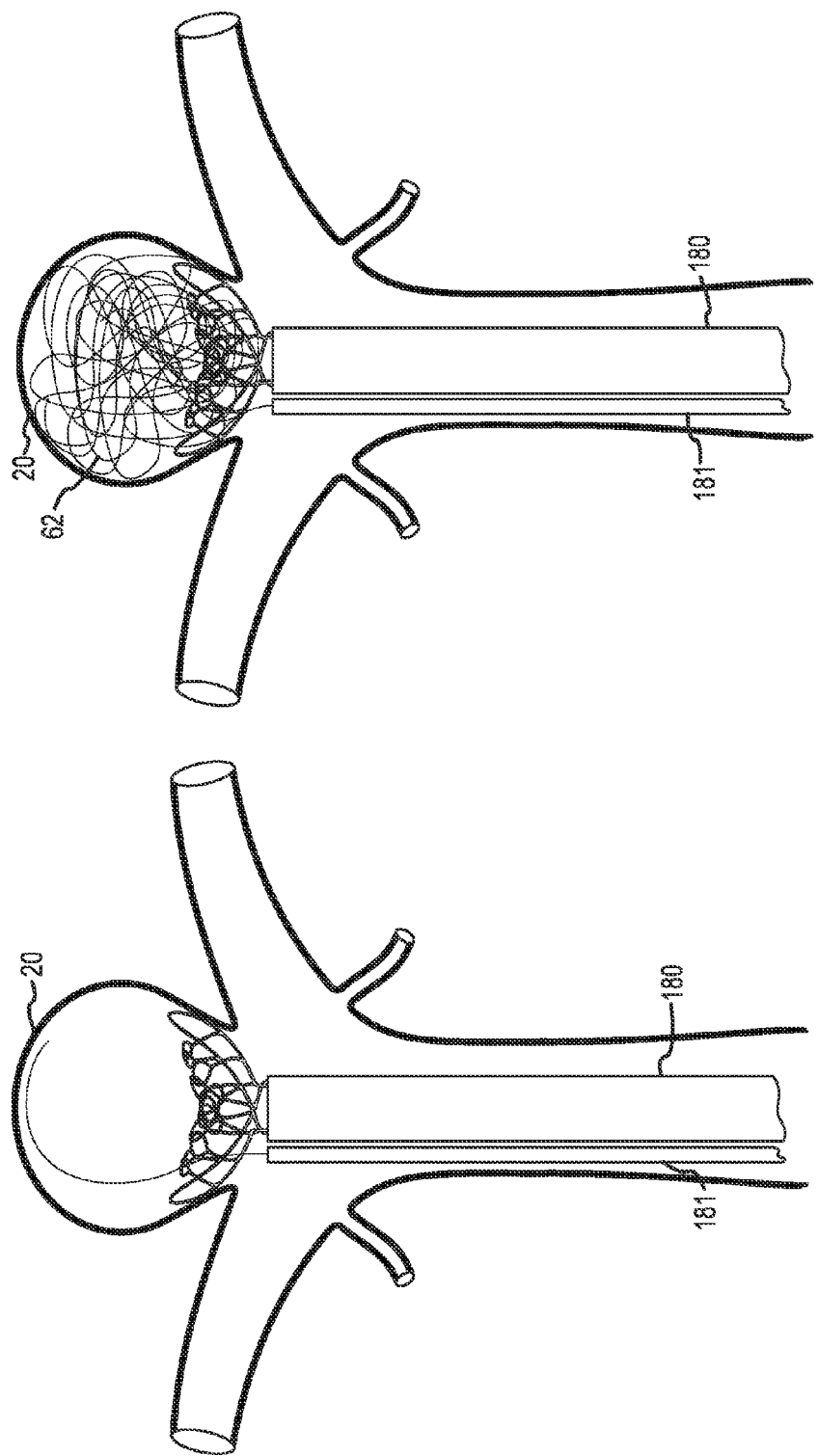

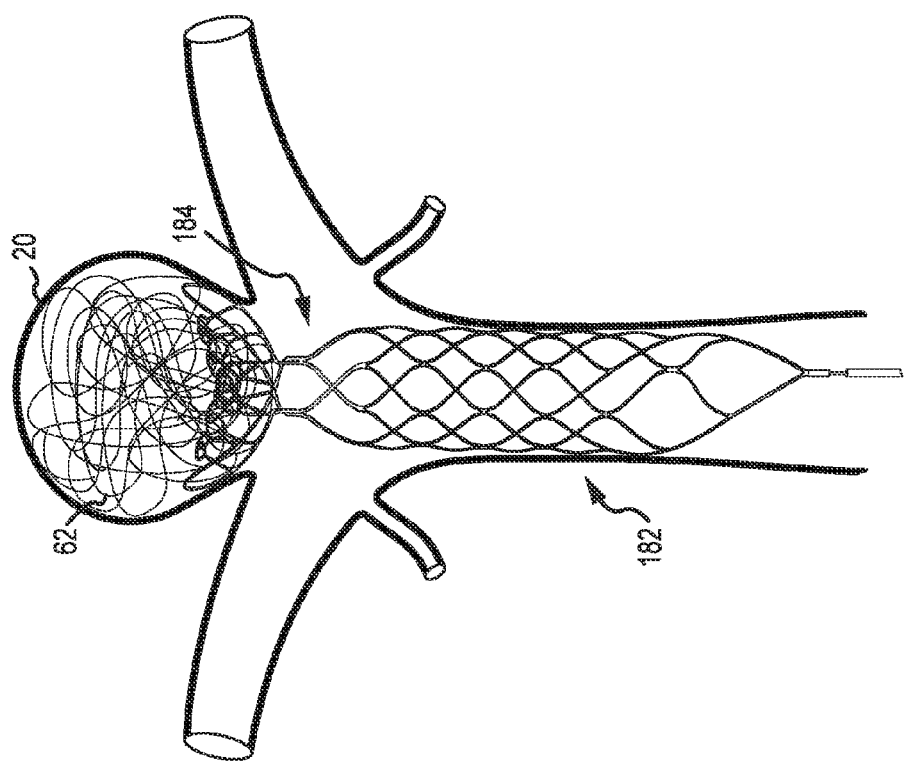

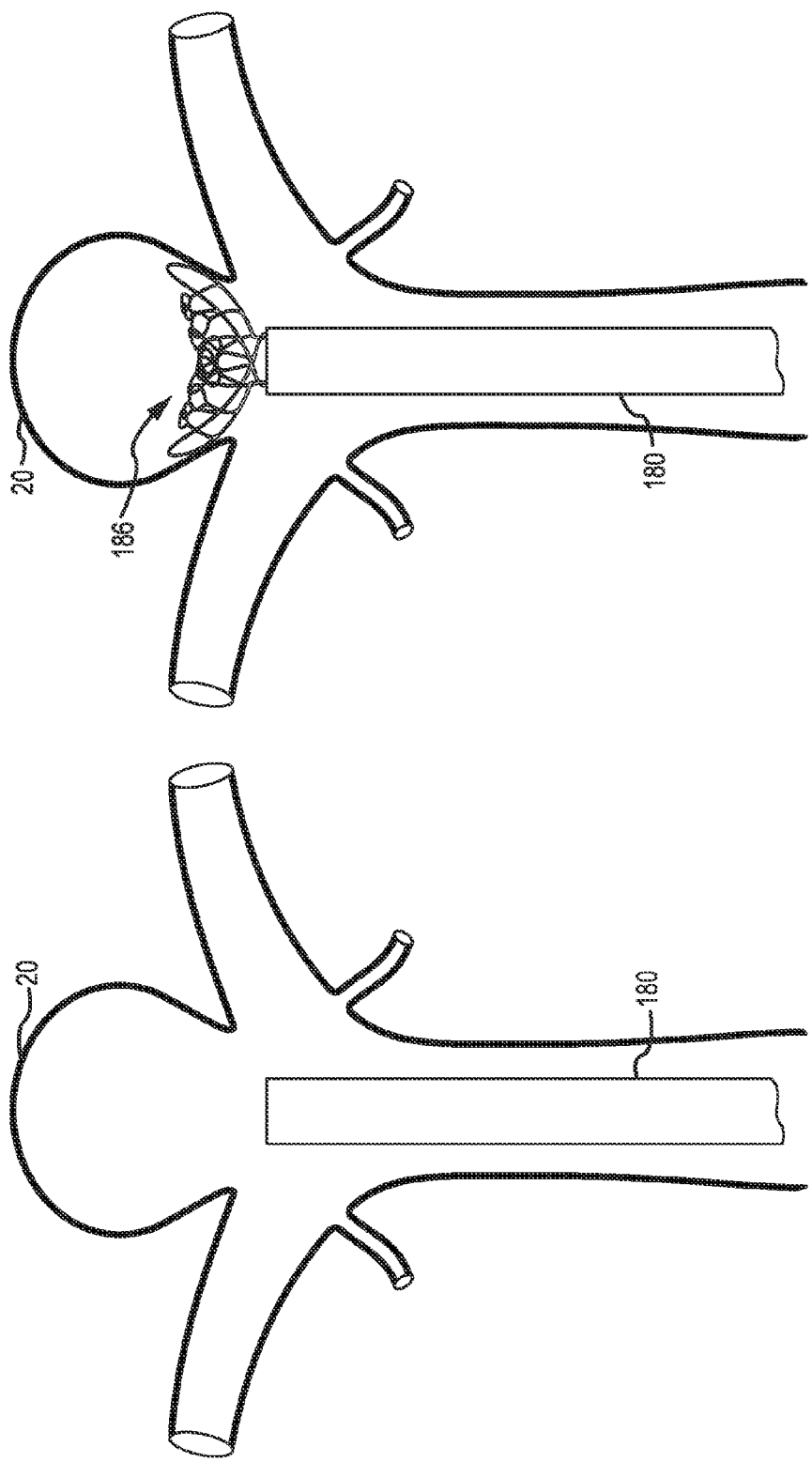

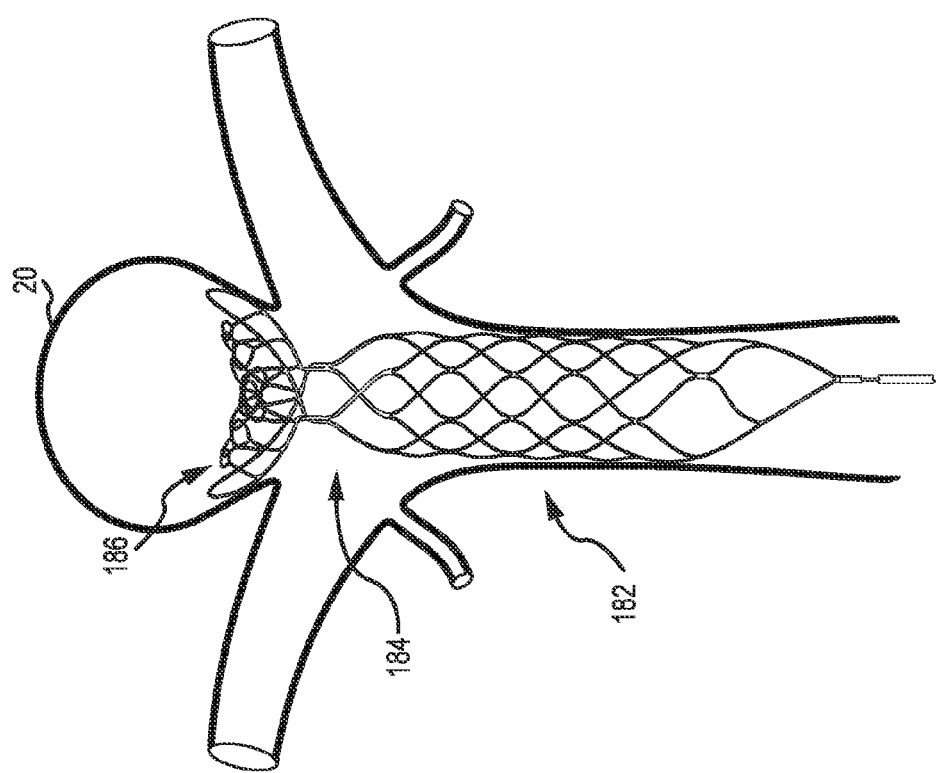

WING BIFURCATION RECONSTRUCTION DEVICE

CROSS-REFERENCE TO RELATED APPLICATIONS

This application is a continuation of U.S. patent application Ser. No. 13/664,648, now U.S. Pat. No. 9,186,276, entitled "WING BIFURCATION RECONSTRUCTION DEVICE," filed on Oct. 31, 2012, the entirety of which is hereby incorporated herein by reference.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, 20 may be treated with embolization coils alone because the coils will generally constrain themselves within the aneurysm 10, 20 without herniating, or being dislodged from the aneurysm, into parent vessels. If the neck ratio is less than 2 to 1 or if the neck 14, 24 is greater than 4 mm, the aneurysms 10, 20 may be difficult to treat with embolization coils alone because the coils may be prone to herniating into parent vessels, as illustrated in FIG. 3A and FIG. 3B. Herniation of coils may cause arterial occlusion, stroke, and/or death. Compared to the bifurcation illustrated in FIG. 2, the efferent vessels of the bifurcation may be at substantially different angles, have substantially different sizes, and/or be a different quantity (e.g., three or more). Compared to the bifurcation illustrated in FIG. 2, the aneurysm 20 of the bifurcation may be offset with respect to the junction (e.g., having a neck substantially open to one efferent vessel), tilted with respect to a plane created by the vessels (e.g., into or out of the page), etc. Moreover, vasculature may include more than two efferent vessels (e.g., three efferent vessels in a trifurcation). Each of these would still be accurately characterized as a "bifurcation" herein.

In order to inhibit such herniation, tubular neck remodeling devices, for example Neuroform®, available from Boston Scientific, and Enterprise™, available from Cordis Neurovascular, may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm. As illustrated in FIG. 4A, tubular remodeling devices 40 are generally useful for side wall aneurysms 10. As illustrated in FIG. 4B and FIG. 4C, tubular remodeling devices 42, 44 are generally less useful for aneurysms 20 at bifurcations (e.g., the basilar tip area), for example because positioning/shaping the remodeling devices to preserve blood flow through the afferent and efferent vessels while also inhibiting herniation of coils 28 out of the aneurysm 20 can be difficult.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into any independent clause, e.g., clause 1 or clause 55. The other clauses can be presented in a similar manner.

1. An intraluminal device comprising:
   a proximal section configured to be positioned and anchored in a blood vessel, the proximal section having a central longitudinal axis;
   a distal section having a first wing extending from a first side of the distal section and a second wing extending from a second side of the distal section, substantially diametrically opposing the first side, the first and second wings being configured to expand from a collapsed state to an expanded state;
   wherein, when the second wing expands to the expanded state, the second wing is configured to extend transverse to the axis from the second side to the first side through an opening in the first wing.

2. The device of clause 1, wherein the proximal section is configured to be positioned and anchored in an afferent vessel.

3. The device of clause 1, wherein, when the second wing expands to the expanded state, the second wing pivots on the first side away from the axis.

4. The device of clause 1, wherein the distal section is configured to act as a scaffolding to inhibit herniation of objects out of a neck of a bifurcation aneurysm and allow perfusion to efferent vessels.

5. The device of clause 1, wherein the proximal section and the distal section each have an outer surface, wherein the outer surface is configured to abut vessel walls and an ostium of an aneurysm without crossing a flow path from an afferent vessel to efferent vessels when the device is placed at a vessel bifurcation.

6. The device of clause 1, wherein the first wing extends from the first side to the second side when expanded.

7. The device of clause 6, wherein, when the first wing expands to the expanded state, the first wing pivots on the second side away from the axis.

8. The device of clause 1, wherein the proximal and distal sections are integrally formed from a tube or sheet.

9. The device of clause 1, wherein the distal section is configured to be placed within the aneurysm when expanded.

10. The device of clause 1, wherein the proximal section is detachably connected to the distal section.

11. The device of clause 1, wherein the device is configured to transition from a compressed state to the expanded state when unrestrained.

12. The device of clause 1, wherein each of the first and second wings comprises a hoop with a plurality of lateral struts connecting opposing sides of the hoop.

13. The device of clause 12, wherein each of the first and second wings comprises a longitudinal strut extending between a pair of lateral struts.

14. The device of clause 1, wherein the distal section comprises a covering.

15. The device of clause 1, wherein the proximal section comprises a substantially cylindrical shape.

16. The device of clause 1, wherein the proximal section comprises a tapered portion.

17. A method of preparing an intraluminal device, comprising:
providing the intraluminal device comprising a proximal section and a distal section, the distal section having (i) a first wing on a first side of the distal section and (ii) a second wing on a second side of the distal section, substantially diametrically opposing the first side;
bending the first wing to extend from the first side to the second side; and
bending the second wing to extend from the second side to the first side through an opening in the first wing.

18. The intraluminal device of clause 17, further comprising providing the intraluminal device with a preset expanded shape corresponding to a vessel bifurcation.

19. The intraluminal device of clause 18, wherein, while in the preset expanded shape, the proximal section is configured to anchor in an afferent vessel and the distal section is configured to allow perfusion to efferent vessels and act as scaffolding to inhibit dislodging of objects out of a neck of a bifurcation aneurysm.

20. The intraluminal device of clause 17, wherein the first wing comprises a first plurality of struts connecting the first wing to the proximal section, and the second wing comprises a second plurality of struts connecting the second wing to the proximal section.

21. The intraluminal device of clause 20, wherein the second plurality of struts are radially inside the first plurality of struts relative to a central longitudinal axis of the proximal section.

22. The intraluminal device of clause 17, wherein providing the intraluminal device comprises forming the intraluminal device integrally from a tubular member or sheet.

23. A method of delivering an intraluminal device comprising:
providing, at a bifurcation aneurysm, the intraluminal device in a compressed state within a sheath, the device comprising (i) a proximal section having a central longitudinal axis, and (ii) a distal section having a first wing on a first side of the distal section and a second wing on a second side of the distal section, substantially opposing the first side, the first and second wings being configured to expand from the compressed state to an expanded state, the second wing being configured to extend from the second side to the first side through an opening in the first wing;
withdrawing the sheath, permitting the intraluminal device to expand from the compressed state to an expanded state, wherein the first wing extends transverse to the axis on the second side and the second wing extends transverse to the axis on the first side.

24. The method of clause 23, wherein when expanding from the compressed state to the expanded state, the proximal section expands radially outward against a wall of an afferent vessel.

25. The method of clause 23, wherein when expanded at the bifurcation, the distal section abuts walls of efferent vessels and spans an ostium of the aneurysm.

26. The method of clause 23, wherein the distal section is positioned within the aneurysm.

27. The method of clause 23, wherein the intraluminal device does not cross a central flow path from an afferent vessel to efferent vessels.

28. The method of clause 23, further comprising delivering an implant through the distal section and into the aneurysm, whereby dislodging of the implant out of the aneurysm is inhibited by the distal section.

29. The method of clause 23, whereby flow into or out of the aneurysm is at least partially diverted.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 1 illustrates an example of a side wall aneurysm.

FIG. 2 illustrates an example of a bifurcation having an aneurysm.

FIG. 3A illustrates an example of a side wall aneurysm with herniating embolization coils.

FIG. 3B illustrates an example of a bifurcation having an aneurysm with herniating embolization coils.

FIG. 4A illustrates a side wall aneurysm treated with embolization coils and a tubular remodeling device.

FIG. 4B and FIG. 4C illustrates a bifurcation having an aneurysm treated with embolization coils and tubular remodeling devices.

FIG. 7A illustrates embodiments of cut patterns in a hypotube for forming the device of FIG. 5A.

FIG. 7B illustrates embodiments of FIG. 7A rotated 90°.

FIG. 8A illustrates embodiments for forming the device of FIG. 5A.

FIG. 8B illustrates embodiments of FIG. 8A rotated 90°.

FIGS. 11A, 11B, 11C, and 11D illustrate embodiments of distal sections of vascular remodeling devices.

FIGS. 12A, 12B, 12C, 12D, 12E, 12F, 12G, 12H, 12I, and 12J illustrate embodiments of proximal sections of vascular remodeling devices.

FIG. 13A and FIG. 13B illustrate embodiments of intermediate sections of vascular remodeling devices.

FIGS. 14A, 14B, 14C, 14D, and 14E illustrate embodiments of methods for treating an aneurysm using a vascular remodeling device.

FIGS. 16A, 16B, and 16C illustrate embodiments of methods for treating an aneurysm using a vascular remodeling device.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

According to embodiments of the present disclosure, a vascular remodeling device may provide therapeutic benefit to vessels containing aneurysms. In particular, a vascular remodeling device of the present disclosure may be placed at a bifurcation of vessels to treat an aneurysm located at the bifurcation. According to embodiments, a vascular remodeling device of the present disclosure may be formed of a single sheet or tube to have opposing wings, wherein one wing is foldable through an opening in the other. When formed in this manner, the device may provide scaffolding to support an implant within the aneurysm or divert flow into or out of the aneurysm. Such treatment may facilitate thrombosis within the aneurysm to reduce a risk of rupture. While the device imparts such treatment to the aneurysm, the device further permits unobstructed flow through parent and branch vessels of a bifurcation.

Figure 5A:
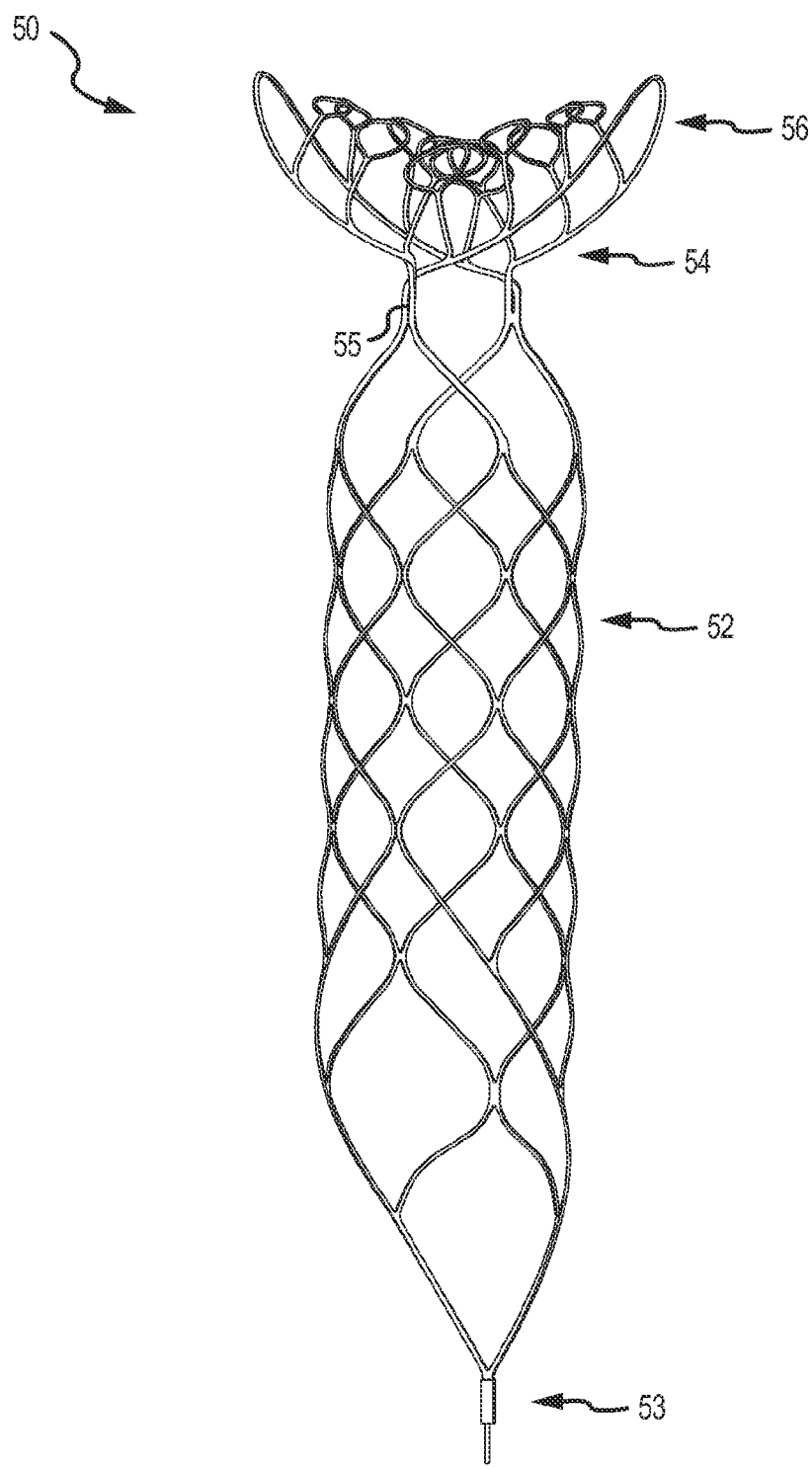
FIG. 5A is a side elevational view of embodiments of a vascular remodeling device.

FIG. 5A illustrates an example embodiment of a vascular remodeling device 50 comprising a scaffolding distal section 56. It will be appreciated that the device 50 may be more compliant than the vasculature in which it is deployed such that it may be somewhat misshapen after being deployed, and that certain shapes described herein are when the device 50 is an expanded (e.g., further expanded) state with no restriction. The device 50 comprises a proximal section 52 (or "bottom section" or "main body" or "tubular portion" or "anchoring section"), an intermediate section 54 (or "middle section" or "open portion" or "flow section"), and a distal section 56 (or "top section" or "distal portion" or "wing section" or "wing portion" or "treatment section"). The device 50 can be delivered via a catheter (e.g., microcatheter, guide catheter, delivery catheter) into a bifurcation to support an aneurysm filling device with minimal or no interruption of blood flow in afferent and efferent vessels. In some embodiments, the device 50 may be retrieved and/or repositioned.

In some embodiments, the intermediate section 54 comprises a plurality of junctures 55. The junctures 55 may be straight, curved, or otherwise shaped, such as having design features like the proximal section 52 with the same or a different cell size. The junctures 55 couple the proximal section 52 to the distal section 56. For example, each juncture 55 may connect to a plurality of struts, with each strut corresponding to a respective wing of the distal section 56. In some embodiments, the intermediate section 54 is a portion of the distal section 56. In some embodiments, the intermediate section 54 is a portion of the proximal section 52. In some embodiments, the junctures 55 have a substantially rectangular or flat cross section (e.g., embodiments, in which the junctures 55 comprise ribbons or uncut portions of a metallic tube or sheet). In some embodiments, the junctures 55 have a substantially round (e.g., circular, elliptical, ovoid) cross section (e.g., embodiments, in which the junctures 55 comprise round filaments). In some embodiments, the plurality of junctures 55 comprises two junctures 55. In some embodiments, the plurality of junctures 55 comprises greater than two junctures 55. In some embodiments, the plurality of junctures 55 comprises between about two junctures 55 and about twelve junctures 55 (e.g., three junctures 55, four junctures 55, five junctures 55, six junctures 55, seven junctures 55, or eight junctures 55). Other numbers of struts are also possible. In certain embodiments, the junctures 55 may be equally spaced and/or oriented on opposite sides of the device 50 (e.g., two struts 180° apart along the circumference of the device 50, three struts 120° apart along the circumference of the device 50, four struts 90° apart along the circumference of the device 50, etc.). When the device 50 is placed at a bifurcation, the intermediate section 54 allows perfusion of blood to efferent vessels because the junctures 55 do not block, obstruct, or cross a flow path of fluid flow in any vessel.

In certain embodiments, the proximal section 52 has a round (e.g., circular, elliptical, or ovoid) cross section. In some embodiments, the proximal section 52 includes filaments having a substantially rectangular or flat cross section (e.g., embodiments, in which the proximal section 52 comprises ribbons or uncut portions of a metallic tube or sheet). In some embodiments, the proximal section 52 includes filaments having a substantially round (e.g., circular, elliptical, ovoid) cross section (e.g., embodiments, in which the proximal section 52 comprises round filaments). In some embodiments, the proximal section 52 comprises a plurality of z-shaped segments coupled by struts. Other patterns of the proximal section 52 are also possible, for example as described with respect to FIGS. 12A-12J. When the device 50 is placed at a bifurcation, the proximal section 52 provides anchoring of the device 50 in the afferent vessel. The proximal section 52 may also facilitate delivery, positioning, retrieval, and/or repositioning of the device 50.

In the example embodiment illustrated in FIG. 5A, the proximal end of the proximal section 52 comprises one or more tapered portions 53. The tapered portion 53 may allow the device 50 or portions thereof (e.g., the proximal section 52) to be retrieved back into a catheter. For example, if the device 50 is being pulled into a catheter, the tapered portions 53 may radially compress the proximal section 52. One tapered portion 53 or other numbers of tapered portion 53 are possible.

Figure 5B:
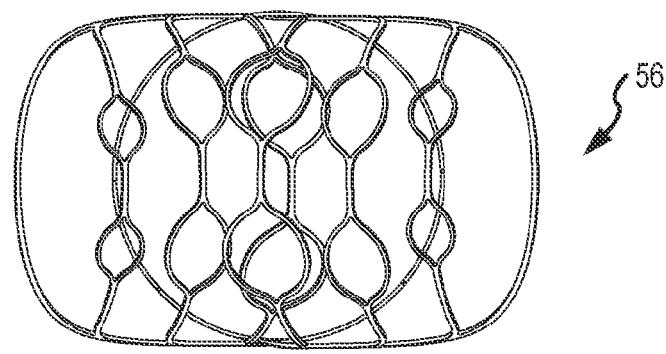
FIGS. 5B, 5C, and 5D are front elevational views of embodiments of distal sections of the vascular remodeling device of FIG. 5A.
Figure 5C:
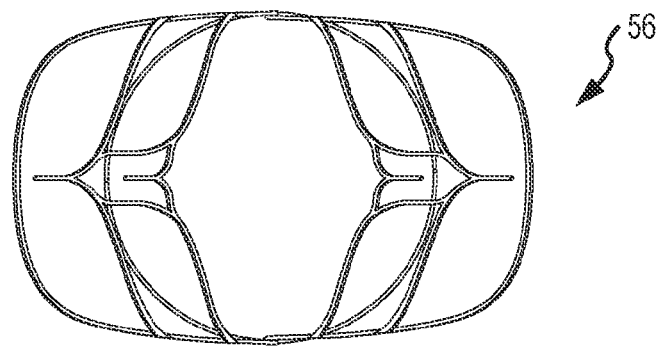
Figure 5D:
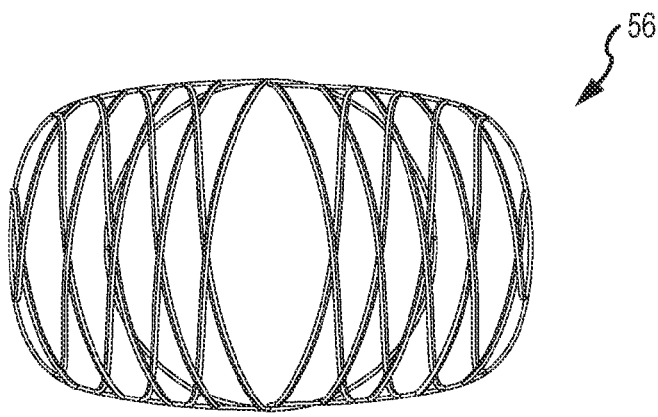

FIGS. 5B-5D illustrate example embodiments of the distal section 56 in a further expanded state. The distal section 56 allows for safe and controlled placement of coils, and can be designed to support a certain packing density of coil. Upon deployment, the distal section 56 can be placed at the neck of an aneurysm and can cover the neck enough that aneurysm filling devices can still be positioned inside the aneurysm. In some embodiments, the distal section 56 comprises one or more of a mesh, a covering, additional filaments, etc. to achieve a fluid diversion effect, which may allow treatment by the omission of embolic material or an aneurysm filling device. The distal section 56 may include radiopaque markers (e.g., coils) around certain filaments. FIG. 5C illustrates the distal section 56 with interconnected filaments. FIG. 5D illustrates the distal section 56 with woven, braided, or mesh members.

In some embodiments, the device 50 comprises a self-expanding (e.g., super elastic, CoCr alloy, polyglycolic acid, polylactic acid, etc.) and/or a shape-memory material (e.g., Nitinol, shape memory polymers, etc.), thereby causing the device 50 to be self-expanding under certain conditions (e.g., not restrained by a catheter). In some embodiments, the proximal section 52, the intermediate section 54, and/or the distal section 56 may comprise different materials. For example, the distal section 56 may comprise polymer material while the proximal section 52 and the intermediate section 54 comprise metallic material, different polymer material, etc. For another example, the distal section 56 may comprise metallic material while the proximal section 52 and the intermediate section 54 comprise different metallic materials, polymer material, etc. Other combinations of materials are also possible. The device 50 can assume a low profile compressed state (e.g., confined within a catheter) for delivery. Upon deployment from the catheter, the device 50 expands (e.g., self-expands) from the compressed state to an expanded state. The distal section 56 expands (e.g., self-expands) to a further expanded state.

Figure 6A:
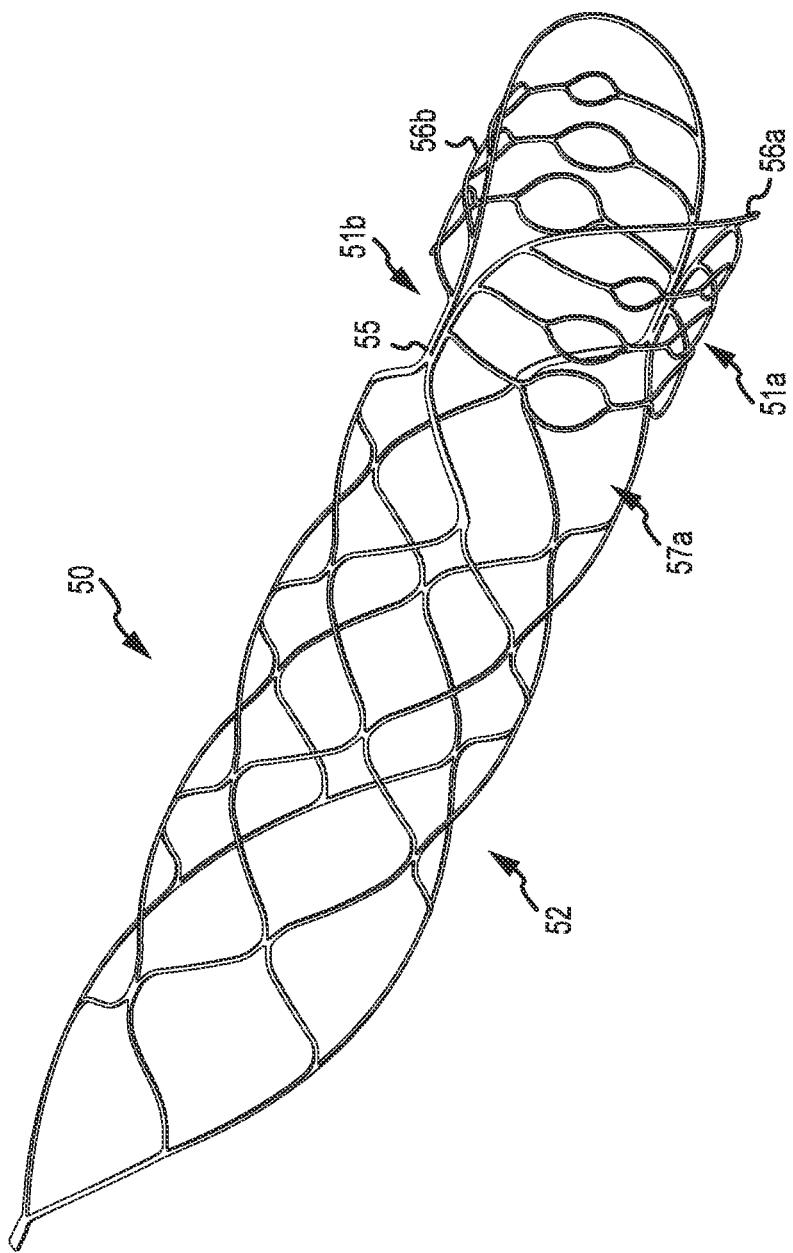
FIGS. 6A, 6B, and 6C illustrate embodiments of further formation of the vascular remodeling device of FIG. 5A.

FIG. 6A-CB illustrate an example embodiment of a vascular remodeling device 50 at various stages of an example manufacturing process comprising shaping a tube (e.g., a laser cut metallic hypotube) or a rolled sheet (e.g., a laser cut metallic sheet). In some embodiments, the device 50 comprises a first wing 56a and a second wing 56b. During at least one stage, the first wing 56a is disposed on a first side 51a of the device 50 and the second wing 56b is disposed on a second side 51b of the device 50. The first side 51a and the second side 51b may be separated by a plane that intersects a juncture 55. The first side 51a and the second side 51b may be separated by a plane that intersects two junctures 55. The first side 51a and the second side 51b may be separated by a plane that intersects a longitudinal axis of the device 50. The first side 51a and the second side 51b may be separated by a plane, within which lies a longitudinal axis of the device 50. The first side Ma may be opposite the second side 51b across a longitudinal axis of the device 50. The first side Ma and the second side 51b may be diametrically opposing.

As shown in FIG. 6A, the first wing 56a may provide a first opening 57a. The first opening 57a may be defined as a passageway through at least a portion of the first wing 56a. The passageway may be substantially orthogonal to the longitudinal axis of the device 50. The first opening 57a may be disposed distal to proximal section 52. The first opening 57a may be disposed proximal to scaffolding elements 59 of the first wing 56a. The first opening 57a may be a region along the first side 51a that is not obstructed by scaffolding elements 59 or any other structure.

In some embodiments, the second wing 56b may also provide a second opening 57b. The second opening 57b may be defined as a passageway through at least a portion of the second wing 56b. The passageway may be substantially orthogonal to the longitudinal axis of the device 50. The second opening 57b may be disposed distal to proximal section 52. The second opening 57b may be disposed proximal to scaffolding elements 59 of the second wing 56b. The second opening 57b may be a region along the second side 51b that is not obstructed by scaffolding elements 59 or any other structure.

Figure 6B:
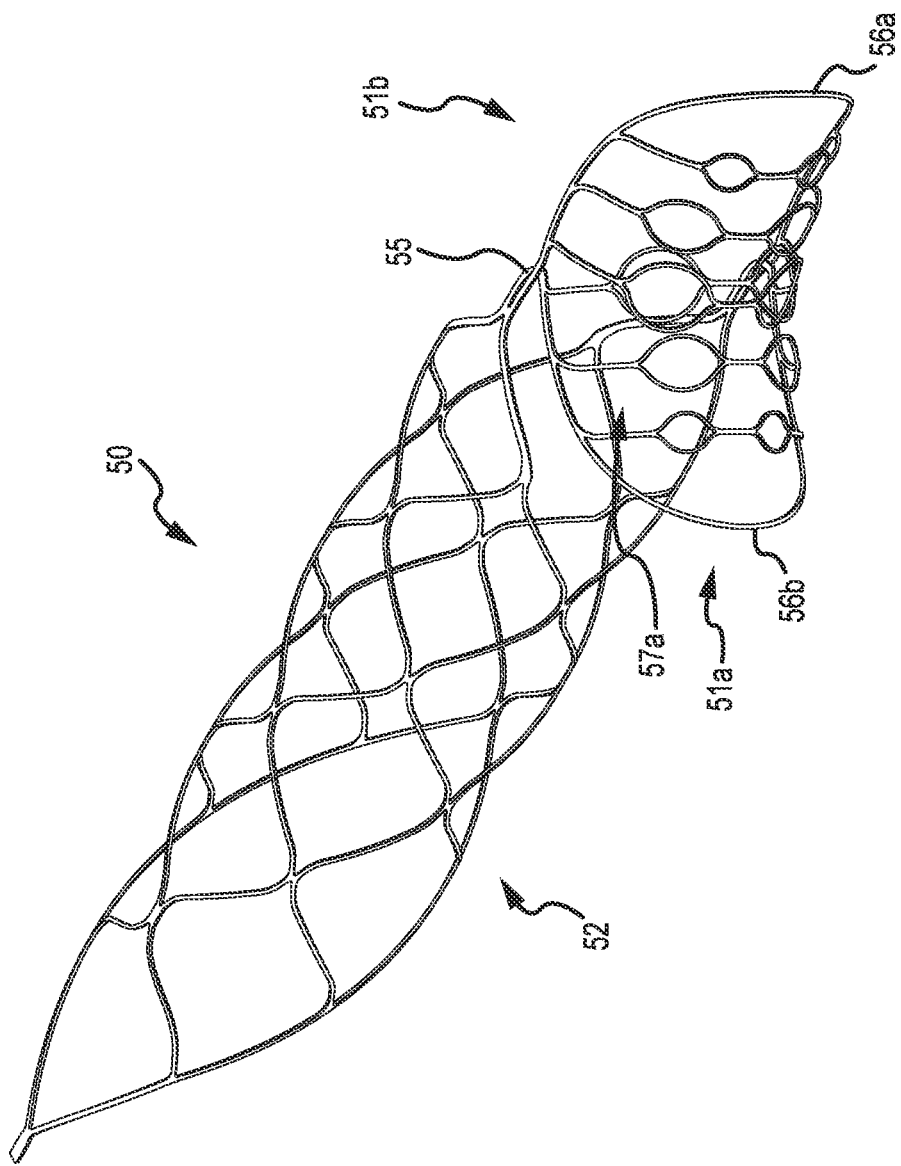

As shown in FIG. 6B, the second wing 56b may be folded through the opening 57a. For example, the second wing 56b may extend from the second side 51b, through the opening 57a, and to the first side 51a. A proximal portion of the second wing 56b may remain on the second side 51b. A distal portion of the second wing 56b may extend to the first side 51a. By further example, when the second wing 56b expands to an expanded state, the second wing 56b is configured to extend transverse to a longitudinal axis of the device 50 from the second side 51b to the first side 51a through an opening 57a in the first wing 56a.

In some embodiments, at least a portion of the second wing 56b is radially within at least a portion of the first wing 56a. As shown in FIG. 6B, at least a portion of a radially outward facing surface of the second wing 56b is in contact with at least a portion of a radially inward facing surface of the first wing 56a.

Figure 6C:
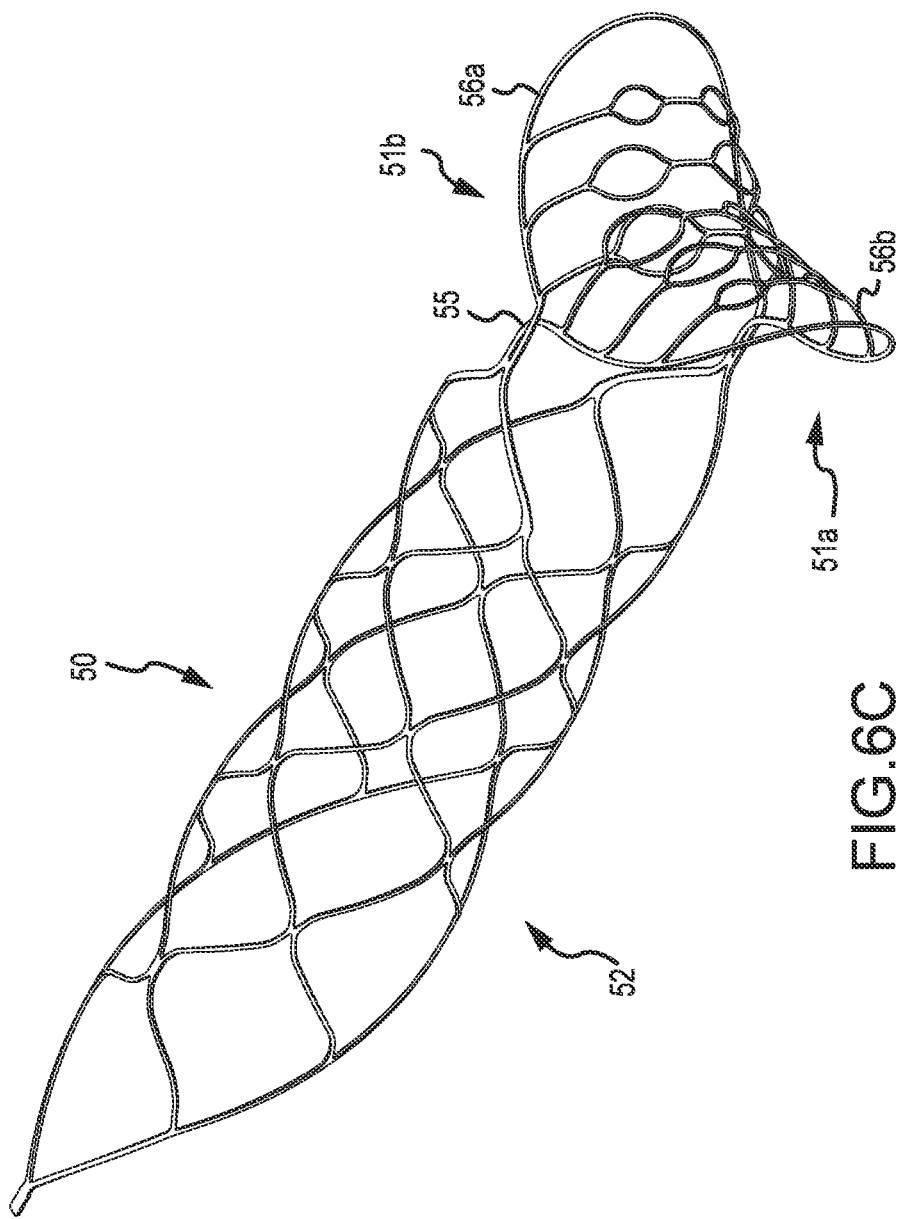

As shown in FIG. 6C, the first wing 56a may also be folded from its initial position as shown in FIG. 6A. For example, the first wing 56a may extend from the first side 51a to the second side 51b. A proximal portion of the first wing 56a may remain on the first side 51a. A distal portion of the first wing 56a may extend to the second side Sib. As further disclosed herein, the device 50 may be subject to a process to provide a temperature-induced or stress-induced condition, to which the device 50 naturally expands in a relaxed state (e.g., to which the device 50 tends to expand when released from a sheath). In some embodiments, with the first wing 56a and the second wing 56b as shown in FIG. 6C, the device 50 may be loaded into a catheter or sheath by radial compression.

FIG. 7A and FIG. 7B illustrate an example embodiment of a vascular remodeling device 50 at various stages of an example manufacturing process comprising shaping a tube (e.g., a laser cut metallic hypotube) or a rolled sheet (e.g., a laser cut metallic sheet), FIG. 7B being rotated 90° with respect to FIG. 7A. A laser may cut out portions of the tube or sheet, leaving a plurality of filaments in the proximal section 52, junctures 55 in the intermediate section 54, and a plurality of filaments in the distal section 56. Other cutting methods (e.g., chemical etch, mechanical cutting, etc.) are also possible.

As shown in FIG. 7A, in some embodiments, one of the first wing 56a and the second wing 56b may be axially longer than the other of the first wing 56a and the second wing 56b. In some embodiments, the first wing 56a and the second wing 56b may have the same axial length. In some embodiments, one of the first wing 56a and the second wing 56b may extend a greater radial distance from a longitudinal axis of the device 50 than the other of the first wing 56a and the second wing 56b. In some embodiments, the first wing 56a and the second wing 56b may extend the same radial distance from a longitudinal axis of the device 50.

As shown in FIG. 7A, in some embodiments, at least one of the first wing 56a and the second wing 56b comprises a hoop, partial hoop, or arc with a plurality of lateral struts extending from opposing sides thereof. In some embodiments, at least one of the first wing 56a and the second wing 56b comprises a longitudinal strut extending between a pair of lateral struts (see FIG. 11C-11D). In some embodiments, the distal section 56 comprises a covering, such as graft material (e.g., polymers, fabrics, etc.).

FIG. 8A and FIG. 8B illustrate an example embodiment of a vascular remodeling device 50 at various stages of an example manufacturing process comprising shaping a tube (e.g., a laser cut metallic hypotube) or a rolled sheet (e.g., a laser cut metallic sheet), FIG. 8B being rotated 90° with respect to FIG. 8A.

As shown in FIG. 8A, in some embodiments, the distal section 56 provides scaffolding or support, at a distal portion thereof, to retain materials within or divert flow from an aneurysm. For example, as shown in FIG. 8A, scaffolding elements 59 of both the first wing 56a and the second wing 56*b* provide a surface configured to be placed at or near the ostium, neck, or opening of an aneurysm.

As shown in FIG. 8B, in some embodiments, the first opening 57*a* and the second opening 57*b* provide one or more flow paths for fluid flow from an afferent vessel to an efferent vessel. In some embodiments, the first opening 57*a* and the second opening 57*b* allow fluid flow in the natural pathway from the afferent vessel to each efferent vessel, without crossing the natural flow path defined by the afferent vessel and each efferent vessel. For example, no part of the device 50 crosses, blocks, impedes, or obstructs the flow path defined by the natural vessels. In some embodiments, the first opening 57*a* and the second opening 57*b* conform to the vasculature, such that every portion of the boundaries of the device 50 defining the first opening 57*a* and the second opening 57*b* abut the vasculature.

In some embodiments, the device 50 comprises a radiopaque material such as platinum, platinum-iridium, and/or tantalum (e.g., being at least partially formed from the radiopaque material (e.g., having a radiopaque layer, consisting of a radiopaque material), including radiopaque markers). For example, the junctures 55 may comprise radiopaque markers. For another example, certain segments of the distal section 56 may comprise radiopaque markers in the form of marker coils and/or marker bands (e.g., as illustrated in FIG. 5C). For yet another example, the junctures 55 and certain segments of the distal section 56 may comprise radiopaque markers. For another example, structural struts in the distal section 56 can themselves comprise (e.g., be made from) a radiopaque material. For still another example, certain segments of the proximal section 52 (e.g., the tapered portions 53, tips of peaks) may comprise radiopaque markers. For another example, structural struts in the proximal section 52 can themselves comprise (e.g., be made from) a radiopaque material. It will be appreciated that the amount and type of radiopaque material used may depend, inter alia, on process technologies, desired level of radiopacity, mechanical properties of the radiopaque material, and corrosion properties of the radiopaque material.

In some embodiments, the device 50 is configured to be positioned at a junction of a bifurcation (e.g., a neurovascular bifurcation (e.g., the basilar tip area)) comprising at least one afferent vessel, efferent vessels, and an aneurysm having a fundus and a neck (e.g., ostium). For example, in some embodiments, the proximal section 52 is suitably dimensioned to fit in an afferent vessel of a bifurcation (e.g., having a diameter between about 2 mm and about 12 mm, having a diameter between about 6 mm and about 8 mm, having a diameter less than about 15 mm, having a diameter greater than about 1 mm). For example, in some embodiments, the proximal section 52 is suitably dimensioned to fit in an afferent vessel of a bifurcation. In certain embodiments, the device 50 is configured to act as a scaffolding to inhibit or prevent herniation or prolapse of objects (e.g., implants, embolization coils, thrombi, etc.) out of a neck of an aneurysm. As used herein, "herniation" refers to relocation of an implant from an implanted location (e.g., within an aneurysm) to a location other than the implanted location (e.g., outside an aneurysm). Herniation may or may not be caused by an external force acting on the coils. For another example, in some embodiments, the distal section 56 is dense enough that such objects cannot pass. In some embodiments, a relative amount of the distal section 56 or a portion thereof occupied by the filaments of the distal section 56 is between about 3% and about 25%. In some embodiments, a relative amount of the distal section 56 or a portion thereof occupied by the filaments of the distal section 56 is between about 3% and about 15%. In some embodiments, a relative amount of the distal section 56 or a portion thereof occupied by the filaments of the distal section 56 is at least about 5%. For another example, in some embodiments, the distal section 56 allows insertion of embolic material therethrough (e.g., through apertures or spaces between struts or filaments). In certain embodiments, the device 50 is configured to permit perfusion of fluid (e.g., blood) to efferent vessels of a bifurcation. For yet another example, in some embodiments, the intermediate section 54 is substantially devoid of a covering, mesh, or other material between the junctures 55, thereby allowing fluid to flow substantially unimpeded.

Figure 9B:
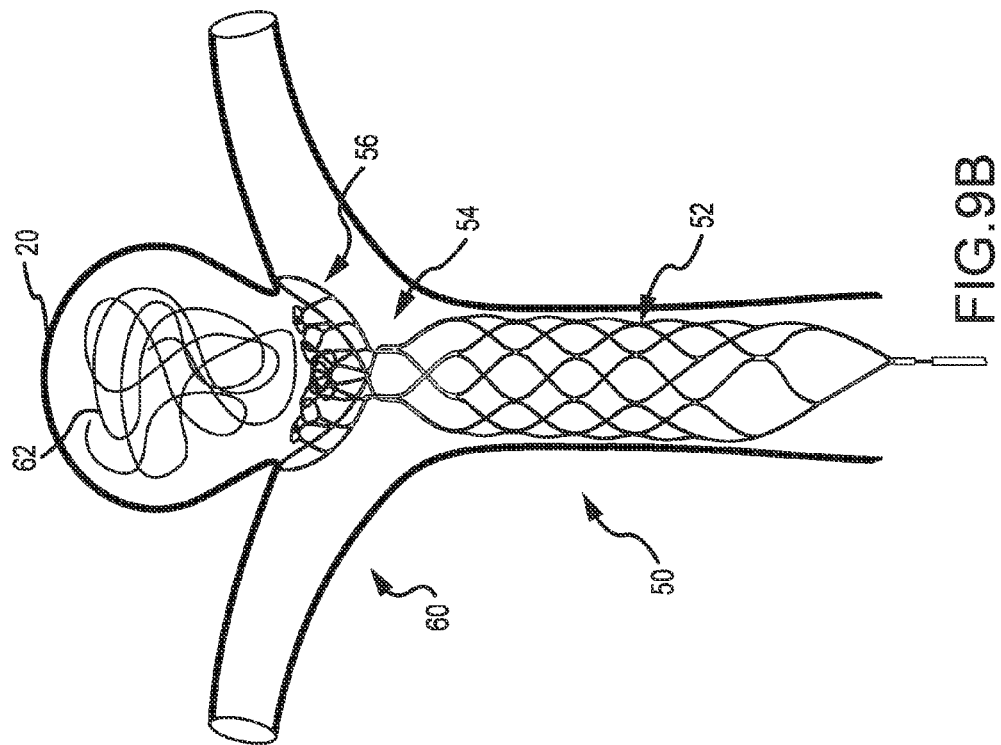
FIG. 9A and FIG. 9B illustrate embodiments of a method for treating an aneurysm using the device of FIG. 5A.
Figure 9A:
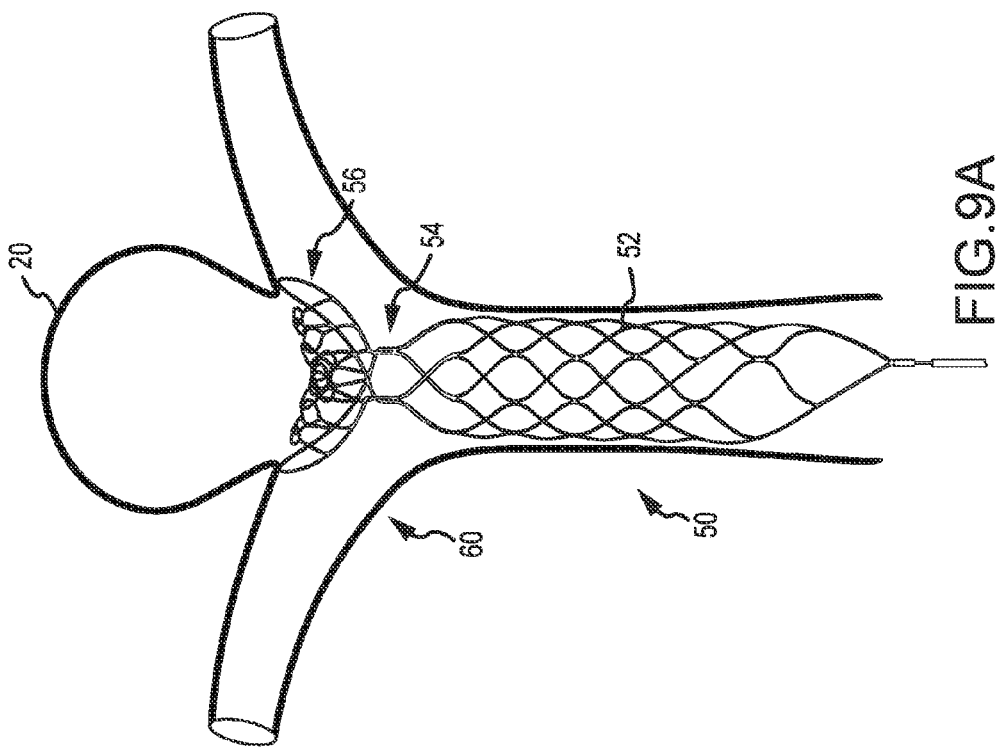

FIG. 9A and FIG. 9B illustrate an example embodiment of a method for treating an aneurysm 20 using the device 50 at a confluence of afferent and efferent vessels or "junction" at a bifurcation 60 having an aneurysm 20. In some embodiments, the vessels are neurovascular or cranial. For example, the vasculature may include the basilar tip aneurysm, the middle cerebral artery, the anterior communicating artery, or the internal carotid bifurcation. In the case of a basilar tip aneurysm, which is at a junction in which the efferent vessels are at about a 90° angle to the afferent vessel, deployment of a conventional aneurysm-bridging stent between the efferent vessels and proximal to the aneurysm neck such that the device can hold embolic material in the aneurysm fundus may be difficult. Treatment of other vasculature, including other than neurovascular or cranial, is also possible.

FIG. 9A shows the proximal section 52 anchored in the afferent vessel and the distal section 56 placed across the neck of the aneurysm 20 after being deployed from a catheter (e.g., by being pushed out with a plunger, by retracting the catheter while the device remains stationary, etc.) and expanding as described herein. In some embodiments, the device 50 comprises a self-expanding and/or a shape-memory material that automatically expands (e.g., self-expands) towards an uncompressed state or does so upon the application of warm fluid (e.g., saline). The junctures 55 of the intermediate section 54 allow fluid flow to the efferent vessels. FIG. 9B illustrates a plurality of embolization coils 62 inserted in the fundus of the aneurysm 20. It will be appreciated that the embolization coils 62 may be a single embolization coil or other embolic material (e.g., embolic fluid such as Onyx®, available from ev3). The embolization coils 62 or other embolic material may be inserted into the fundus before or after positioning of the device 50. In some embodiments, the embolization coils 62 are inserted in the fundus of the aneurysm 20 using the same catheter from which the device 50 is deployed. In some embodiments, the embolization coils 62 are inserted in the fundus of the aneurysm 20 using a different catheter than the catheter from which the device 50 is deployed. In certain such embodiments, a guidewire may be used to guide both catheters. The device 50 acts as a scaffolding to inhibit or prevent herniation or prolapse of objects such as the embolization coils 62 and/or thrombi out of the aneurysm 20. The distal section 56 of the device 50 may allow insertion of embolic material therethrough. The device 50 also allows perfusion of fluid (e.g., blood) from the afferent vessel(s) to the efferent vessel(s). If the position of the device 50 is not ideal or preferred, it can be pulled back inside the delivery catheters, repositioned, and redeployed at a different (e.g., better) position.

As shown in FIGS. 9A and 9B, in some embodiments, the proximal section 52 and the distal section 56 define an outer surface of the device 50, the outer surface being configured to abut vessel walls of the afferent and efferent vessels and an ostium of the aneurysm 20 without crossing a flow path from the afferent vessel to the efferent vessels. In some embodiments, the device 50 is deployed in the parent vessel for treating a bifurcation aneurysm, and the device 50 is configured not to reside in the path of direct blood flow after being deployed.

In some embodiments, final release of the device 50 is mechanical (e.g., by a release mechanism). In some embodiments, release of the device 50 is electrolytic (e.g., by applying a small current until a proximal tip of the tapered portions 53 corrodes away). In some embodiments, final release of the device 50 is chemical (e.g., by dissolving a connecting portion with a biocompatible solvent such as DMSO). The delivery systems and catheter may then be withdrawn from the bifurcation 60, thereby leaving or permanently positioning the device 50 at the junction of the bifurcation 60.

Figure 10B:
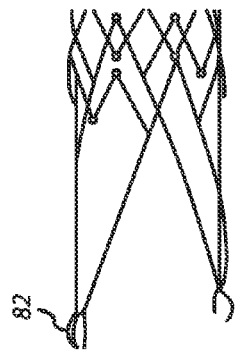
FIGS. 10A, 10B, and 10C illustrate embodiments of vascular remodeling device detachment mechanisms.
Figure 10C:
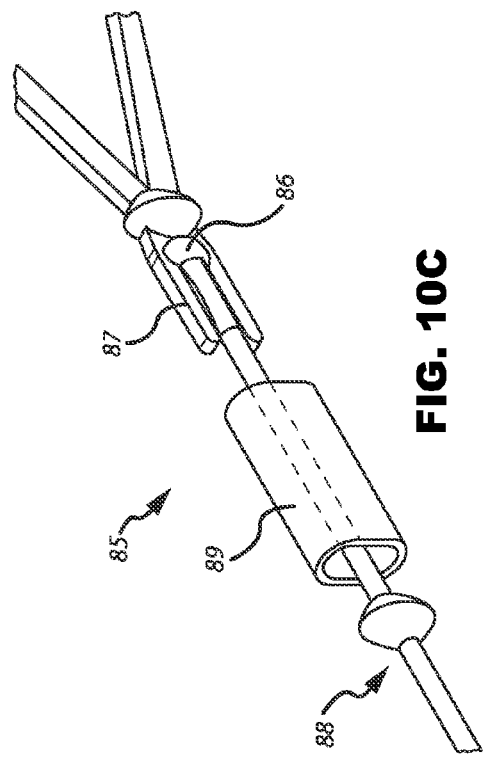
Figure 10A:
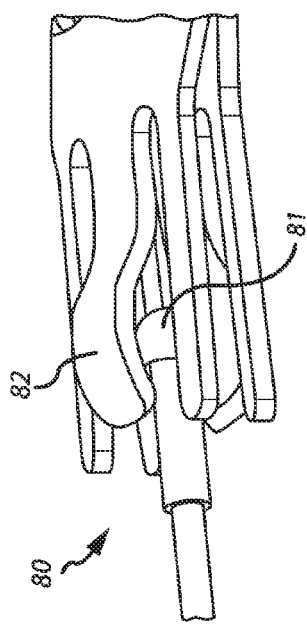

FIGS. 10A-10C illustrate example embodiments of release mechanisms that may be used to decouple the device 50 from a pusher wire or other portion of a delivery catheter. These and other release mechanisms may also be used for other devices described herein. In some embodiments, the release mechanism comprises a corrodible wire (e.g., for electrolytic detachment). In some embodiments, the release mechanism comprises a chemically reactive substance (e.g., dissolvable by DMSO). In some embodiments, the release mechanism comprises a mechanical release mechanism.

FIG. 10A illustrates a release mechanism 80 comprising a guidewire or catheter portion comprising an expanded end portion 81 (having a larger diameter than the portion proximal thereto) and a device proximal end portion comprising a plurality of fingers 82. When the device is confined within a catheter, the compression of the device material causes the fingers 82 to lock around the expanded end portion 81 and to couple the device proximal end portion to the guidewire or catheter portion. The device may optionally be released by causing the device proximal end to exit the catheter (e.g., by pushing a guidewire and/or pulling a catheter), at which point the fingers 82 may flex outwardly and lose grip on the expanded portion 81 (e.g., as illustrated in FIG. 10B). Alternatively, the device proximal end portion may comprise the expanded portion 81 and the guidewire or catheter portion may comprise the plurality of fingers 82.

FIG. 10C illustrates an example embodiment of an electrolytic release mechanism 85 comprising interlocking pieces 86, 87. A guidewire or a catheter portion comprises the piece 86 and the device proximal end portion comprises the piece 87, although a reverse configuration and other piece shapes are also possible. Unlike the expanded end portion 81 and the fingers 82 of the embodiment of FIG. 10A and FIG. 10B, the interlocking pieces 86, 87 are not configured to be released from each other. Although illustrated as proximal to the pieces 86, 87, a marker band 89 may surround the pieces 86, 87. The device may optionally be released by applying an electrical current and causing a narrow portion 88 of the device (e.g., proximal (e.g., immediately proximal) to the "bumper" or "glue dome") to dissolve, thereby releasing the distal end portion of the guidewire or the catheter portion and the device. In embodiments comprising a marker band 89, the marker band 89 may also be released from the guidewire or catheter portion and remain with the device by being distal to the narrow portion 88.

In some embodiments, the distal portion 56 is detachable from the proximal portion 52. For example, the distal portion 56 may be detached from the proximal portion 52 using one or more of the mechanisms described herein with respect to FIG. 10A-10C. By further example, the distal portion 56 may be delivered such that at least a portion thereof abuts, spans, or covers an ostium of an aneurysm. For example, the distal portion 56 may be deployed at an intra-saccular or an extra-saccular location. The distal portion 56 may be detached at a location proximal to one or more junctures 55, such that the first wing 56a and the second wing 56b remain connected to the one or more junctures 55. In some embodiments, the distal portion 56 is detachably connected to a delivery wire at or near one or more junctures 55.

It will be appreciated that the term "permanently" does not mean that the device 50 is impossible to remove and/or reposition at a later time. In some embodiments, the delivery catheter or a different catheter may be used to retrieve or reposition the device 50. In certain embodiments, the device 50 may be retracted into a catheter after being deployed. The device 50 may then be repositioned, for example, at a new rotational position, more proximal or distal to an afferent vessel and/or an efferent vessel, etc, or may be completely removed from the body, for example prior to delivery of a new device (e.g., a different device 50). Once the user is satisfied with the repositioned properties of the device 50 (e.g., size, position, rotation, shape, interaction with the vessels, etc.), the device 50 may be released.

FIGS. 11A-D illustrate example embodiments of a vascular remodeling device 50 at various stages of an example manufacturing process comprising cutting a sheet (e.g., a laser cut metallic sheet). In some embodiments, the device 50 may be formed from a cut sheet (e.g., according to a cut pattern) and rolled to form a substantially cylindrical shape. The rolled sheet may have overlapping portions in a radially compressed or radially expanded state. The rolled sheet may have opposing sides that are attached to form the substantially cylindrical shape.

In some embodiments, at least one of the first wing 56a the second wing 56b are formed with scaffolding elements 59. The scaffolding elements 59 may elastically deformed to provide flexibility with respect to the first opening 57a and the second opening 57b.

In some embodiments, as shown in FIG. 11A, scaffolding elements 59a may include lateral struts that extend across each of the first wing 56a and second wing 56b. Each of the lateral struts may include openings where one portion of a strut divides into two struts. The two struts may then join together again into one strut along the lengths thereof. This configuration may increase the distribution of scaffolding elements when deployed across an ostium of an aneurysm.

Figure 11B:
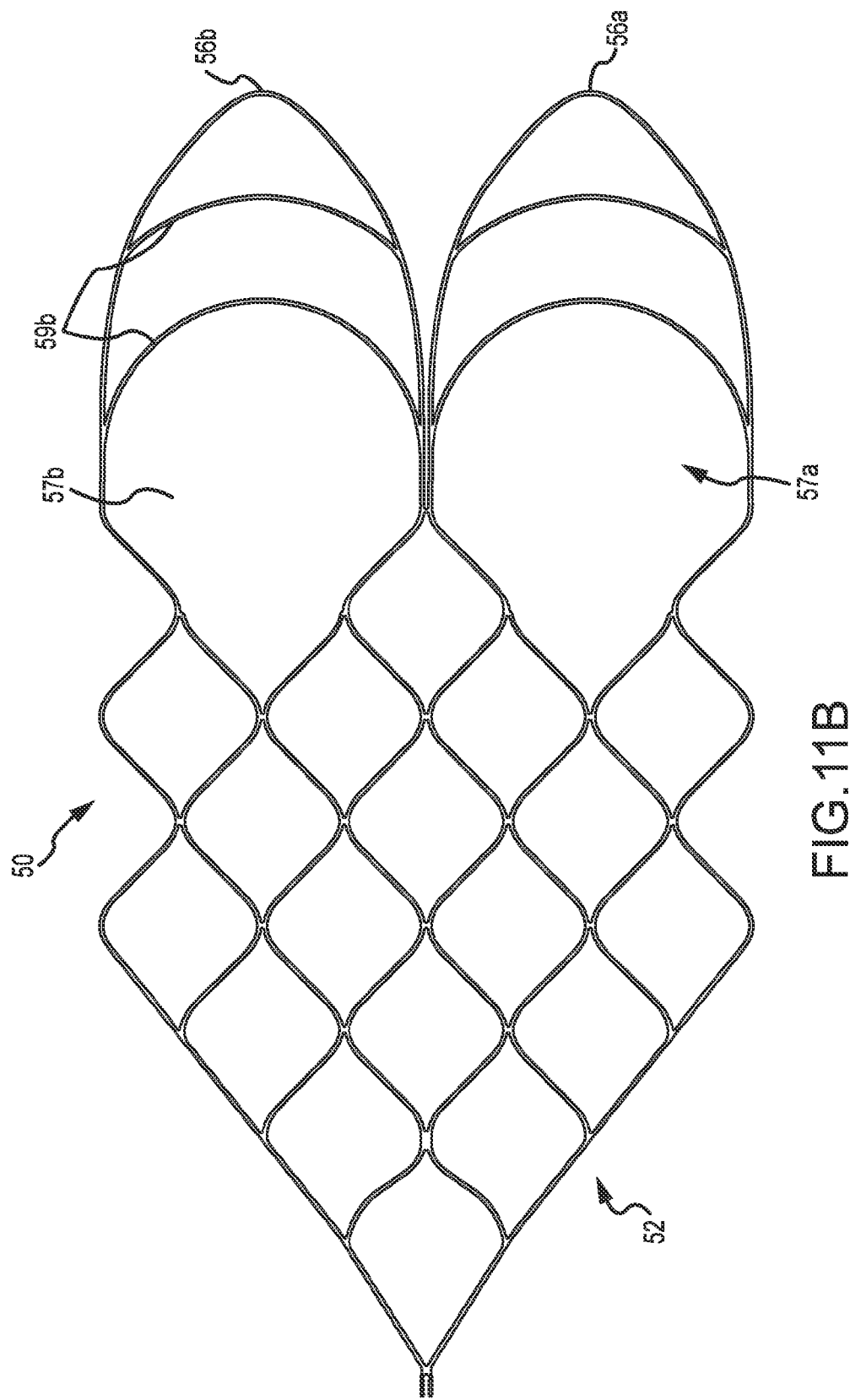

In some embodiments, as shown in FIG. 11B, scaffolding elements 59b may include struts extending across each of the first wing 56a and second wing 56b. The struts may form a curve or arc relative to a longitudinal axis of the device 50 when cut from a sheet. The struts may form parallel or nonparallel curves.

Figure 11C:
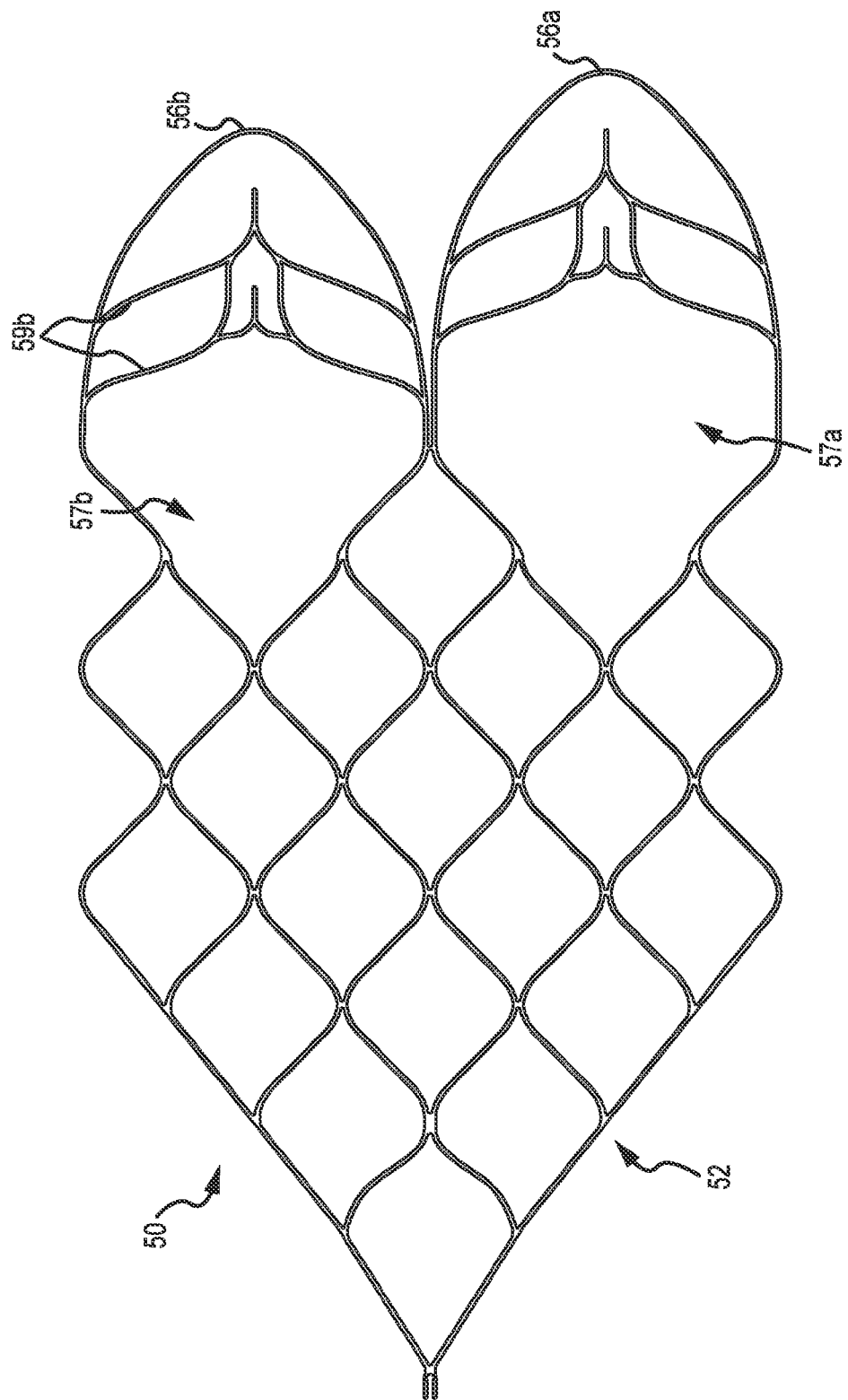

In some embodiments, as shown in FIG. 11C, scaffolding elements 59c may include lateral struts and a longitudinal struts interconnecting the lateral struts. As further shown in FIG. 11C, at least some of the struts may have terminal ends that do not connect to the outer hoop of the first wing 56a or the second wing 56b.

Figure 11D:
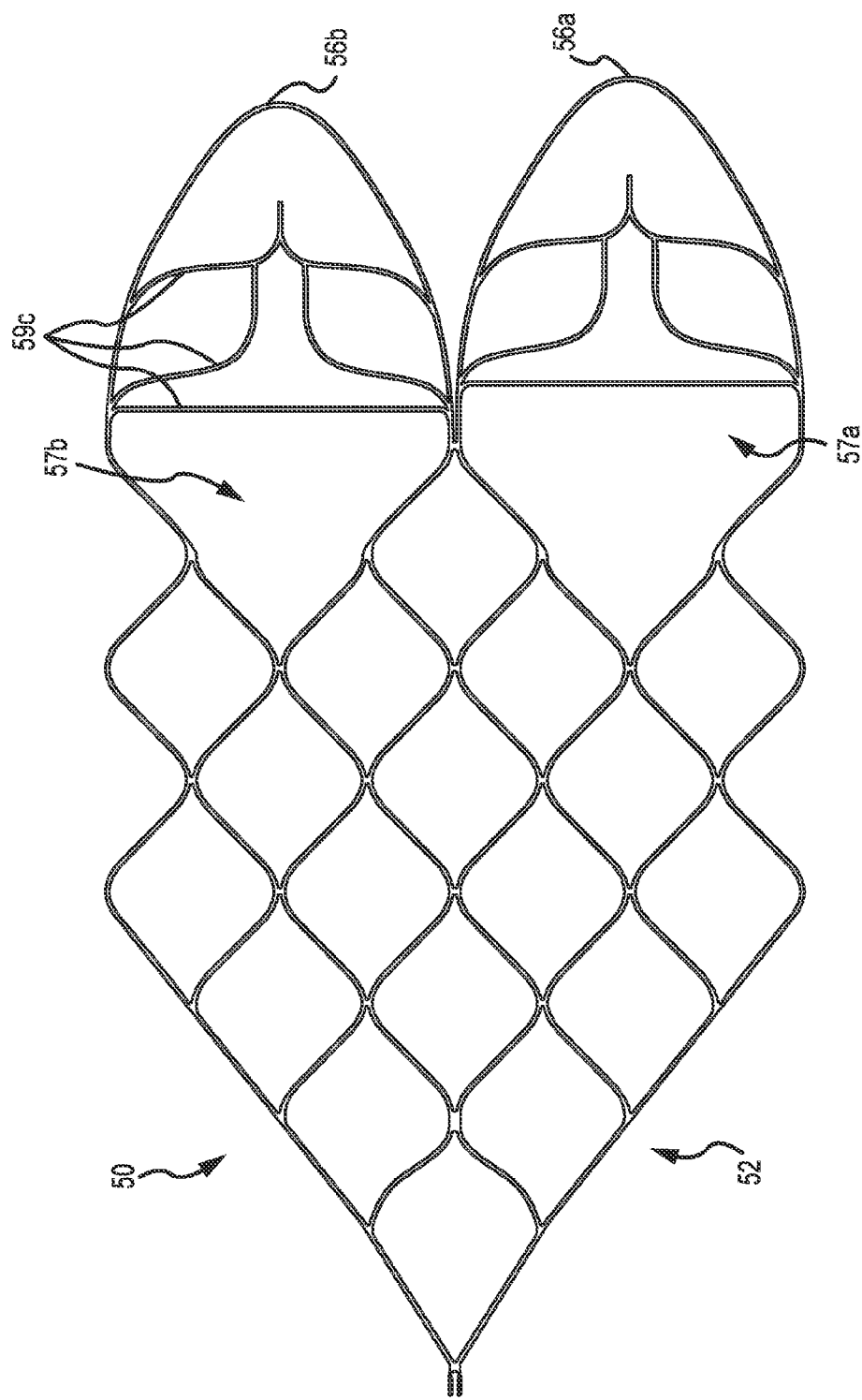

In some embodiments, as shown in FIG. 11D, scaffolding elements 59d may include some struts having curvature and other struts being substantially linear when cut from a sheet. It should be appreciated that struts are given a new and different curvature when rolled from a sheet to a substantially cylindrical configuration.

FIGS. 12A-12J illustrate example embodiments of proximal sections 1221, 1222, 1223, 1224, 1225, 1226, 1227, 1228, 1229, 1230 that may be incorporated into the devices described herein. FIG. 12A illustrates an example embodiment of a proximal section 1221 having an "open cell" design, identifiable by the reverse free-peaks 124 and the forward free-peaks 125. Open cell designs generally provide good flexibility and wall apposition, but may be difficult to retrieve, for example due to reverse free-peaks snagging or catching on the catheter during retrieval. FIG. 12B illustrates an example embodiment of a proximal section 1222 having a "closed cell" design, identifiable by the lack of any peaks due to contact of all cells at intersections 126. FIG. 12C illustrates another example embodiment of a proximal section 1223 having a "closed cell" design, identifiable by the lack of reverse free-peaks 127 and forward free-peaks 128, which are connected by struts 129. Closed cell designs are generally easy to deliver and to retrieve, but may be stiff and provide poor wall apposition (e.g., being prone to kinking rather than bending).

At least one aspect of the subject technology is the realization that a hybrid of open cell and closed cell designs can advantageously incorporate the advantages of each design and can avoid the potential drawbacks of each design. FIGS. 12D-12H illustrate example embodiments of proximal sections that are "hybrid" or "combination" designs including features of open cell designs and features of closed cell designs. FIG. 12D illustrates an example embodiment of a proximal section 1224 having a hybrid cell design. The proximal section 1224 comprises forward connected peaks 131 and 133, forward free-peaks 132, and reverse connected peaks 134. The forward peaks 133 are connected to the next unit cell. The proximal section 1224 does not include any reverse free-peaks (124 of FIG. 12A). FIG. 12E illustrates an example embodiment of a proximal section 1225 having a hybrid cell design. The proximal section 1225 comprises forward connected peaks 131 and 133, forward free-peaks 132, and reverse connected peaks 134. The forward peaks 133 are connected to the next unit cell. The proximal section 1225 does not include any reverse free-peaks (124 of FIG. 12A). FIG. 12F illustrates an example embodiment of a proximal section 1226 having a hybrid cell design. The proximal section 1226 comprises forward connected peaks 131, forward free-peaks 132, and reverse connected peaks 134. The proximal section 1226 further comprises valleys 135 connected to the next unit cell. The proximal section 1226 does not include any reverse free-peaks (124 of FIG. 12A). FIG. 12G illustrates an example embodiment of a proximal section 1227 having a hybrid cell design. The proximal section 1227 comprises forward connected peaks 131, forward free-peaks 132, and reverse connected peaks 134. The proximal section 1227 further comprises valleys 135 connected to the next unit cell. The proximal section 1227 does not include any reverse free-peaks (124 of FIG. 12A).

FIG. 12H illustrates an example embodiment of a proximal section 1228 having a hybrid cell design. The proximal section 1228 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1228 further comprises peaks connected to the next unit cell. The proximal section 1228 does not include any reverse free-peaks (124 of FIG. 12A). FIG. 12I illustrates an example embodiment of a proximal section 1229 having a hybrid cell design. The proximal section 1229 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1229 further comprises peaks connected to the next unit cell. The proximal section 1229 does not include any reverse free-peaks (124 of FIG. 12A). In contrast to the proximal section 1228 of FIG. 12H, the proximal section 1229 of FIG. 12I has fewer diagonal struts (e.g., missing in the area 138), which may provide better flexibility and/or wall apposition. FIG. 12J illustrates an example embodiment of a proximal section 1230 having a hybrid cell design. The proximal section 1230 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1230 further comprises peaks connected to the next unit cell. The proximal section 1230 does not include any reverse free-peaks (124 of FIG. 12A). In contrast to the proximal section 1229 of FIG. 12I, the proximal section 1230 of FIG. 12J has straight struts 1391, which may be less prone to twisting during compaction. Combinations of the features of the cell patterns illustrated in FIGS. 12A-12I may be selected based on desired properties of the proximal section.

FIG. 12B, FIG. 12D, and FIG. 12F illustrate proximal sections 1222, 1224, 1226, respectively, having one tapered section 123, while FIG. 12A, FIG. 12C, FIG. 12E, FIG. 12G, FIG. 12H, FIG. 12I, and FIG. 12J illustrate proximal portions 1221, 1223, 1225, 1227, 1228, 1229, 1230, respectively, having two tapered sections 123. A single tapered section 123 may advantageously have only one detachment zone and be easy to release, while a plurality of tapered sections 123 may comprise a detachment zone proximal to each tapered section 123 and may be more difficult to release. A plurality of tapered sections 123 may be more symmetrical and provide more uniform wall apposition. A plurality of tapered sections 123 may have less of a tension effect on the vessel, which may result from a single long tapered area applying force to a single side of the vessel. The effective length of the proximal section may be based on the intended anatomy. Longer lengths may be appropriate for more vessel wall apposition, while shorter lengths may be appropriate for traversing more tortuous anatomy. In some embodiments, the effective length of the proximal section is between about 5 mm and about 40 mm. In some embodiments, the effective length of the proximal section is between about 10 mm and about 30 mm. In some embodiments, the effective length of the proximal section is between about 10 mm and about 20 mm. Other effective lengths are also possible.

FIG. 12C, FIG. 12F, and FIG. 12G illustrate proximal sections 1223, 1226, 1227, respectively, comprising s-shaped struts 129 connecting certain forward peaks and reverse peaks. FIG. 12D, FIG. 12E, and FIG. 12J illustrate proximal portions 1224, 1225, 1230, respectively, comprising straight struts 1391 connecting certain forward peaks and reverse peaks. FIG. 12H and FIG. 12I illustrate proximal portions 1228, 1229 comprising c-shaped struts 1392 connecting certain forward peaks and reverse peaks. Connection struts having an s-shape or c-shape may be more flexible, but may be prone to twisting during compaction, while straight struts may be easier to compress but less flexible, which may be acceptable for hybrid cell designs already having suitable flexibility.

FIG. 12D and FIG. 12E illustrate proximal sections 1224, 1225 having tip-to-tip connections between forward and reverse peaks, which may provide a smaller compaction profile. FIG. 12F, FIG. 12G, FIG. 12H, and FIG. 12I illustrate proximal sections 1226, 1227, 1228, 1229 having at least partially offset tip-to-tip connections between forward and reverse peaks, which may provide increased flexibility and/or may increase vessel conformance.

FIG. 12D, FIG. 12E, FIG. 12H, FIG. 12I, and FIG. 12J illustrate proximal sections 1224, 1225, 1228, 1229, 1230, respectively, having tip-to-tip connections between forward and reverse peaks of unit cells, which may provide an easier compaction profile. FIG. 12F and FIG. 12G illustrate proximal sections 1226, 1227 having valley-to-tip connections between forward and reverse peaks of unit cells, which may provide good flexibility.

Figure 4C:
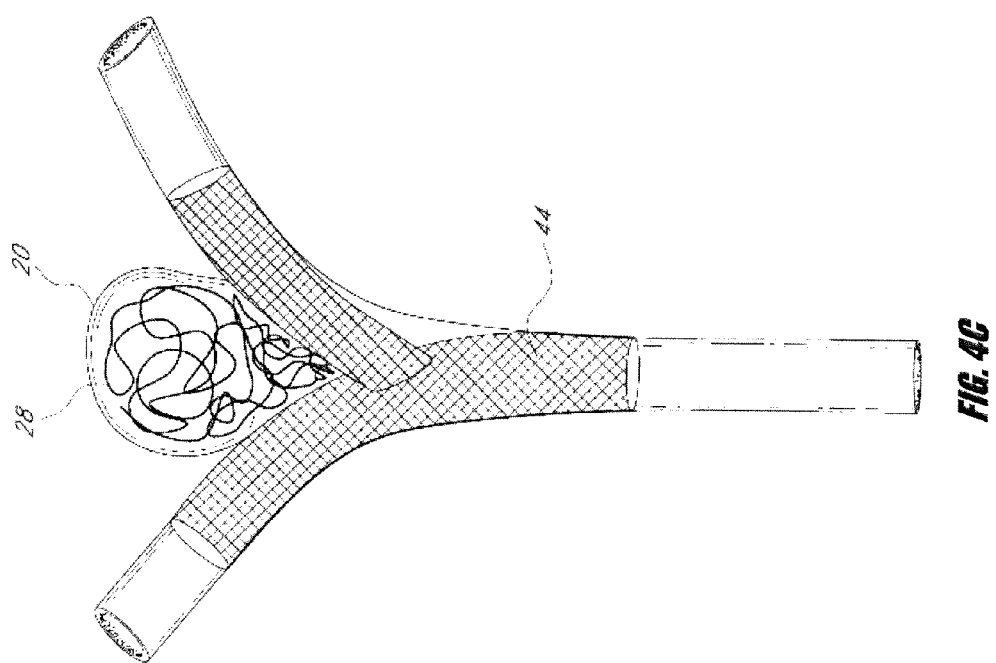

The patterns described herein can be repeated (e.g., repetition of rows of unit cells), adjusted (e.g., different angles, different lengths, different thicknesses, etc.), and/or combined (e.g., permutations of any of the features disclosed herein) based on the desired properties of the proximal section. In some embodiments, the proximal section may be flow diverting, which may allow the device to be used across sidewall aneurysms, for example as shown in FIG. 4A. In some embodiments, radiopaque markers are integrated into a portion (e.g., the distal peaks of the forward free-peaks, around the struts, etc.) of the proximal section that the user (e.g., physician) can use to monitor placement of the device.

FIG. 13A and FIG. 13B illustrate example embodiments of intermediate sections 1341, 1342 that may be incorporated into the devices described herein. FIG. 13A illustrates an example embodiment of an intermediate section 1341 comprising a plurality of straight struts 125. The number of struts 125 may be selected, for example, based on the expected weight of the embolic coils. For example, as coil weight increases, the number of struts 125 may increase. In some embodiments, the plurality of struts 125 comprises two struts 125. In some embodiments, the plurality of struts 125 comprises greater than two struts 125. In some embodiments, the plurality of struts 125 comprises three struts 125 (e.g., as illustrated in FIG. 13A). In some embodiments, the plurality of struts 125 comprises between about two struts 125 and about twelve struts 125 (e.g., three struts 125, four struts 125, five struts 125, six struts 125, seven struts 125, or eight struts 125). Other numbers of struts 125 are also possible. In some embodiments, the struts 125 may be equally spaced and/or oriented on opposite sides of the device (e.g., two struts 180° apart along the circumference of the device, three struts 120° apart along the circumference of the device, four struts 90° apart along the circumference of the device, etc.).

FIG. 13B illustrates an example embodiment of an intermediate section 1342 comprising a straight strut 125 and two elongation struts 137 comprising openings. During compaction, the openings of the elongation struts 137 may collapse, thereby increasing the length of the elongation struts 137. In an example embodiment illustrated in FIG. 13B, upon compaction the straight strut 125 would maintain length, the middle elongation strut 137 would increase in length somewhat, and the top elongation strut 137 would increase in length the most. The portions of the distal section attached to the strut 125 and elongation struts would be differentiated, which may provide a good compaction profile.

Any combination or permutation of the proximal, intermediate, and distal sections described herein, whether in FIGS. 12A-13 or elsewhere, may be used in an intraluminal device for aneurysm treatment or other uses. It will be appreciated that a large number of permutations are possible by selecting a proximal section from amongst FIGS. 12A-12G (or equivalents or modifications thereof), selecting an intermediate section from amongst FIG. 13A and FIG. 13B (or equivalents or modifications thereof), and/or selecting a distal section from amongst FIGS. 11A-11D (or equivalents or modifications thereof). Thus, the devices disclosed herein are not limited to any explicitly illustrated embodiment.

The proximal section, the intermediate section, and the distal section may be integrally formed from the metallic tube or sheet and not cut away from each other. In embodiments in which all sections of the device are integrally fabricated by being cut from the same tube or sheet, the device is of single-piece construction. Single-piece construction may allow for easier manufacturing.

In some embodiments, some or all of the proximal section, the intermediate section, and the distal section may be formed separately, and the parts coupled together (e.g., by being welded, glued, adhered, mechanically crimped, mechanically swaged, braided, physical vapor deposited, chemical vapor deposited, etc.). For example, the proximal section and the distal section may be cut from a tube or a sheet and then coupled (e.g., welded, glued, adhered, mechanically crimped, mechanically swaged, braided, physical vapor deposited, chemical vapor deposited, etc.) by the struts (e.g., welded, glued, adhered, mechanically crimped, mechanically swaged, braided, physical vapor deposited, chemical vapor deposited, etc.).

Certain portions of the proximal section, the intermediate section, and the distal section may be formed separately. For example, a proximal end segments may be cut from a tube or a sheet and then coupled (e.g., welded, glued, adhered, mechanically crimped, mechanically swaged, braided, physical vapor deposited, chemical vapor deposited, etc.) by connectors. In some embodiments, the distal section may comprise different material than the proximal section. For example, the distal section may comprise platinum, platinum-iridium, or a polymer and the proximal section may comprise Nitinol or CoCr alloy. Other combinations of materials are also possible. Separate or multiple-piece construction may allow for independent selection of materials that are suited for the intended use.

In some embodiments, some parts of the distal section (e.g., peaks) are integrated with the proximal section (e.g., being cut from the same tube or sheet) and other parts of the distal section (e.g., struts between peaks) are formed separately from the proximal portion and are attached (e.g., welded, glued, adhered, mechanically crimped, mechanically swaged, braided, physical vapor deposited, chemical vapor deposited, etc.). Combination construction may allow easier fabrication than purely multiple-piece construction and also some material selection advantages.

After cutting the tube or the sheet, the device may be reshaped and the device may be heat treated to impart shape setting to at least the distal section and/or the proximal section 122. The shape setting process may include several steps comprising, for example, successively shapes using appropriate tooling to stretch and confine the cut tube into a new shape during the heat treatment. At the end of the each heat treatment step, the cut tube or sheet assumes the shape in which it was confined during the heat treatment process. The final shape (e.g., further expanded state) and size may obtained by several such steps. In some embodiments in which a cut sheet is rolled to form a tube, there may be a slit along the length of the device (e.g., the opposite sides of the sheet are not joined), or the edge(s) can be welded or otherwise joined together by other methods to form a complete tubular profile. In certain such embodiments, the sides may be in contact or spaced.

FIGS. 14A-14E illustrate an example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 14A shows a catheter 180 (e.g., microcatheter) positioned in the afferent vessel and projecting into the bifurcation. FIG. 14B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline).

As shown in FIG. 14C and FIG. 14D, a second catheter 181 can be used to insert embolic coils 62 in the aneurysm 20 while the proximal section 182 of the device remains in the catheter 180. It will be appreciated that the embolization coils 62 may be a single embolization coil or other embolic material (e.g., embolic fluid such as Onyx®, available from ev3). The device can act as a scaffolding to inhibit or prevent herniation or prolapse of objects such as the embolization coils 62 and/or thrombi out of the aneurysm 20. The second catheter 181 is then removed, and the catheter 180 is removed to deploy the proximal section 182 in the afferent vessel. The device also allows perfusion of fluid (e.g., blood) from the afferent vessel(s) to the efferent vessel(s).

Figure 15B:
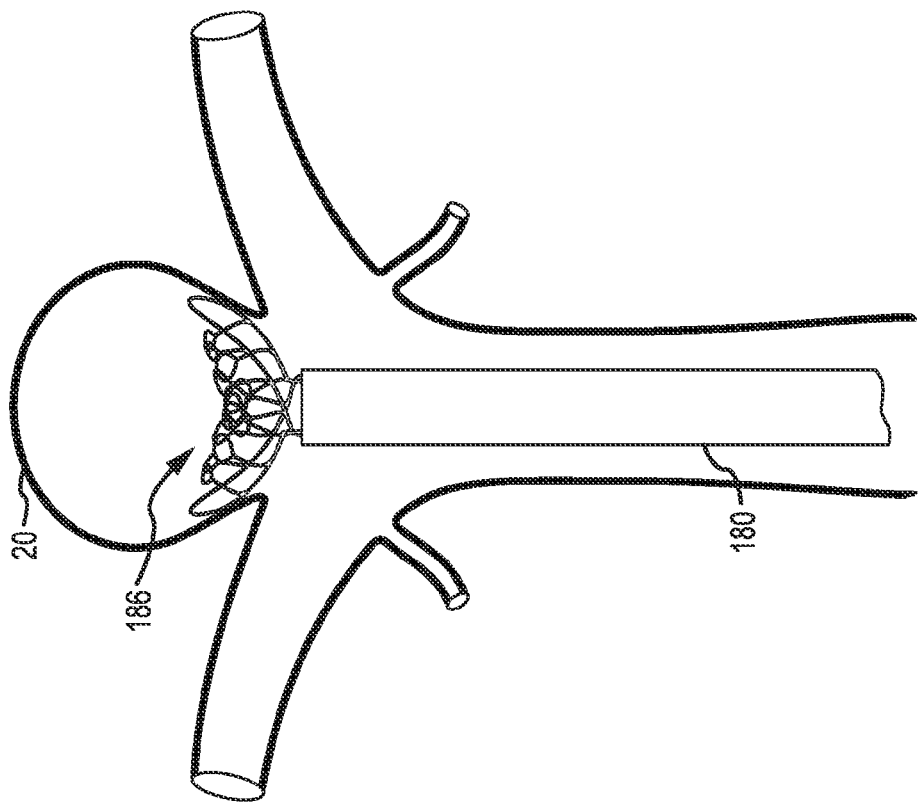
FIGS. 15A, 15B, 15C, 15D, and 15E illustrate embodiments of methods for treating an aneurysm using a vascular remodeling device.
Figure 15A:
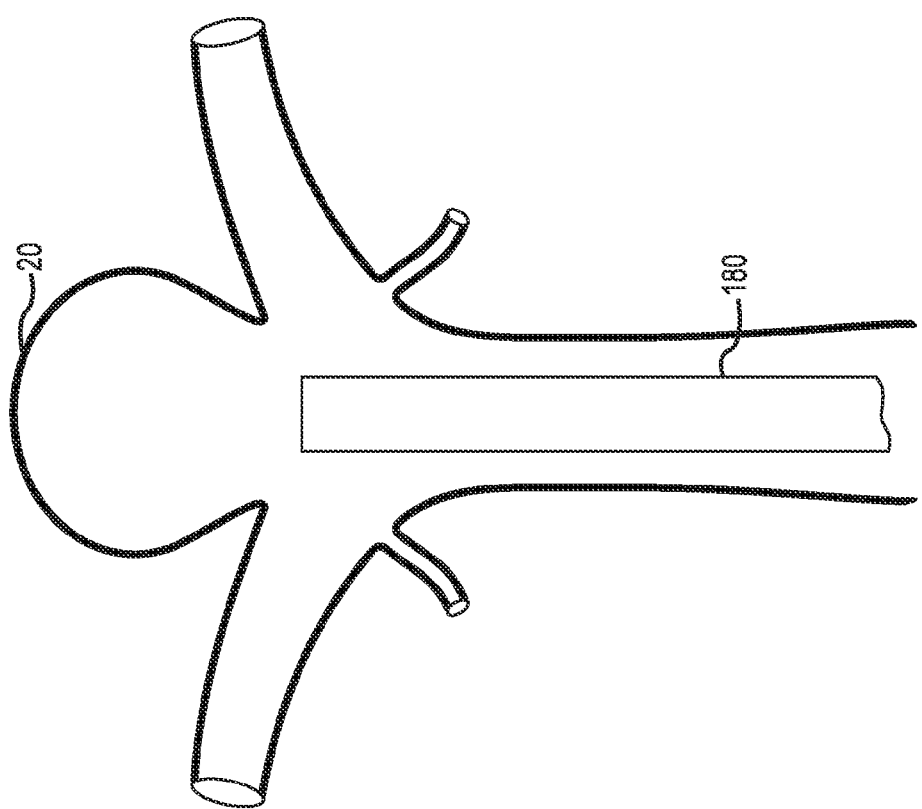
Figure 15C:
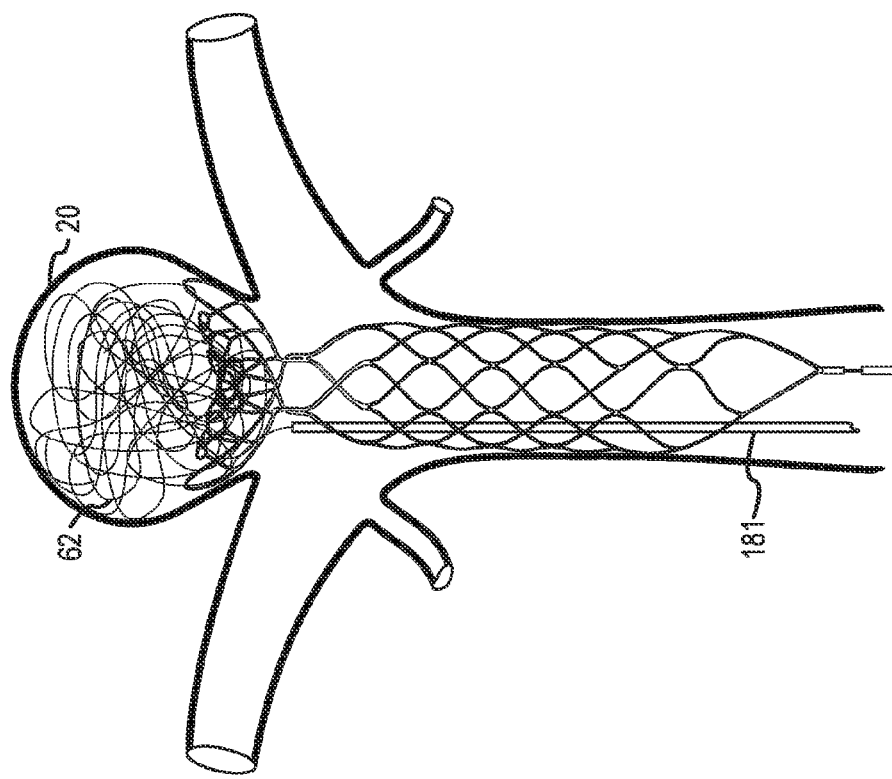
Figure 15D:
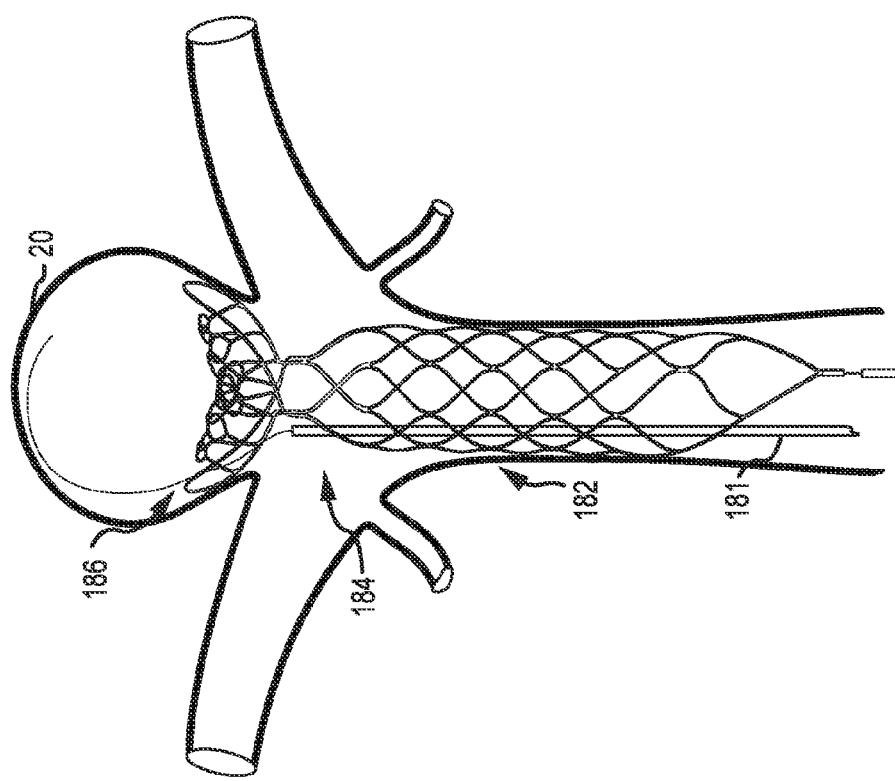
Figure 15E:
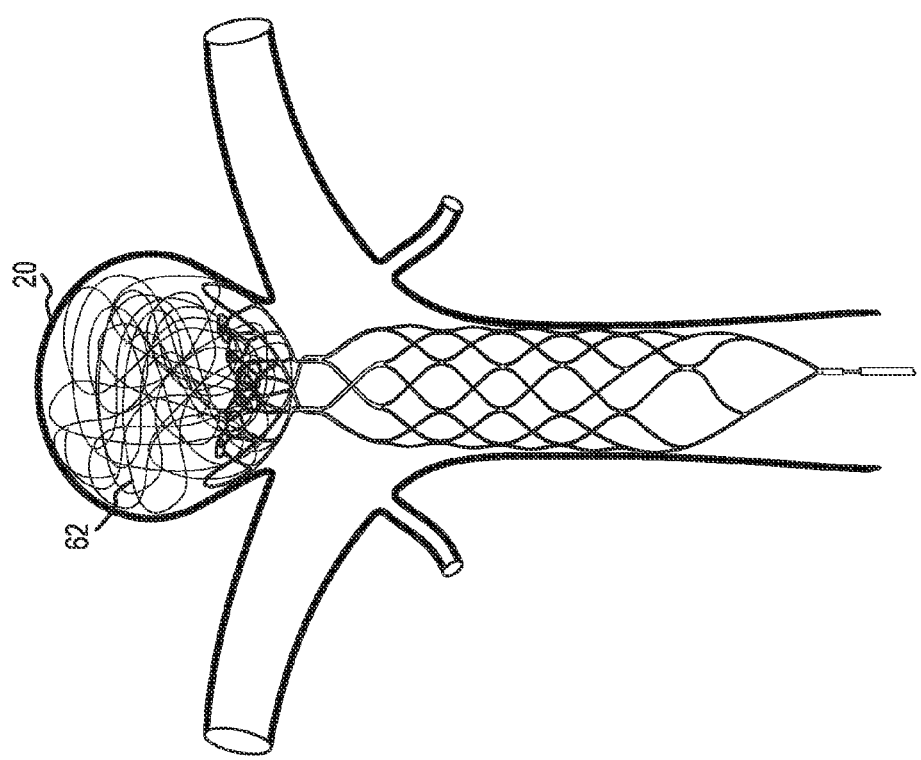

FIGS. 15A-15E illustrate another example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 15A shows a catheter 180 (e.g., microcatheter) positioned in the afferent vessel and projecting into the bifurcation. FIG. 15B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline). FIG. 15C shows the entire device including the proximal section 182 being released from the catheter 180 and the catheter 180 being removed prior to inserting a second catheter 181. The proximal section 182 anchors the device in the afferent vessel. As shown in FIG. 15C and FIG. 14D, a second catheter 181 is used to insert embolic coils 62 in the aneurysm 20. It will be appreciated that the embolization coils 62 may be a single embolization coil or other embolic material (e.g., embolic fluid such as Onyx®, available from ev3). The device can act as a scaffolding to inhibit or prevent herniation or prolapse of objects such as the embolization coils 62 and/or thrombi out of the aneurysm 20. The second catheter 181 is then removed. The device also allows perfusion of fluid (e.g., blood) from the afferent vessel(s) to the efferent vessel(s).

FIGS. 16A-16C illustrate yet another example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 16A shows a catheter 180 (e.g., microcatheter) positioned in the afferent vessel and projecting into the bifurcation. FIG. 16B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline). FIG. 16C shows the entire device including the proximal section 182 being released from the catheter 180 and the catheter 180 being removed prior. The proximal section 182 anchors the device in the afferent vessel. In contrast to the methods described with respect to FIGS. 14A-15E, a second catheter is not used to insert embolic material in the aneurysm 20. Rather, the embodiment of the device used in the method of FIGS. 16A-16C either comprises a porosity or covering that can divert fluid flow. The device also allows perfusion of fluid (e.g., blood) from the afferent vessel(s) to the efferent vessel(s).

Certain devices described herein may be advantageously used to treat aneurysms having a neck ratio (a ratio of fundus width to neck width) greater than about 2 to 1 and/or a neck width greater than about 4 mm. In treatment of such aneurysms, embolization coils may be prone to herniating into parent vessels because the size and/or shape of the aneurysm is not conducive to maintaining the coils in their inserted locus. In some embodiments, embolization coils are inserted in the fundus of the aneurysm after positioning a generally spherical device so that the embolization coils do not have an opportunity to herniate. It will be appreciated that certain devices described herein may also be used to treat aneurysms having a neck ratio less than about 2 to 1 and/or a neck width less than about 4 mm. In some embodiments, embolization coils are inserted in the fundus of the aneurysm before positioning a generally spherical device.

In some embodiments in which embolic material was previously inserted in an aneurysm but has herniated, certain devices described herein may be used as a "rescue device" to push the herniated material back into the aneurysm and to act as a scaffolding to inhibit or prevent further herniation or prolapse of the embolic material. In certain such embodiments, deployment of such devices may advantageously avoid traversal of the junction comprising the herniated material by wires or a catheter (e.g., there is no need to traverse wires or a catheter past the junction into an efferent vessel for positioning of the device as is generally needed to position tubular devices such as the devices 42, 44 illustrated in FIG. 4B and FIG. 4C), which may cause the herniated material to become tangled and/or dislodged and which may cause rupture of the aneurysm.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the term "and" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, and C" includes at least one of only A, of only B, of only C, of any combination of A, B, and C; and/or of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method of delivering an intraluminal device comprising:
    positioning the intraluminal device within a body vessel while in a compressed state, the intraluminal device comprising (i) a proximal section, (ii) a distal section having (a) a first wing including first base struts connected to each other by a first end strut and (b) a second wing including second base struts connected to each other by a second end strut, and (iii) at least two junctures between the proximal section and the distal section, wherein the first wing and the second wing are fixedly connected to each other only at the at least two junctures;
    expanding the intraluminal device from the compressed state to an expanded state in which (i) the first base struts extend from different ones of the at least two junctures and along a first side of the distal section and the first end strut is on a second side of the distal section, substantially opposing the first side, (ii) the second wing extends through an opening in the first wing, and (iii) the second base struts extend from different ones of the at least two junctures and along the second side and the second end strut is on the first side.

2. The method of claim 1, wherein the intraluminal device is positioned within the body vessel while within a sheath, and wherein the expanding comprises withdrawing the sheath.

3. The method of claim 1, wherein the expanding comprises expanding the proximal section radially outwardly against a wall of an afferent vessel.

4. The method of claim 1, wherein the expanding comprises positioning the distal section to abut walls of efferent vessels.

5. The method of claim 1, wherein, after the expanding, the intraluminal device does not cross a central flow path from an afferent vessel to efferent vessels.

6. The method of claim 1, wherein the expanding the intraluminal device comprises expanding the distal section at an aneurysm.

7. The method of claim 6, wherein the expanding the intraluminal device comprises expanding the distal section to span an ostium of the aneurysm.

8. The method of claim 6, wherein the expanding the intraluminal device comprises expanding at least a portion of the distal section to extend within the aneurysm.

9. The method of claim 6, further comprising delivering an implant through the distal section and into the aneurysm, whereby dislodging of the implant out of the aneurysm is inhibited by the distal section.

10. The method of claim 6, wherein, after the expanding, flow into or out of the aneurysm is at least partially diverted.

11. A method of delivering an intraluminal device comprising:
   positioning the intraluminal device in a body vessel, the intraluminal device comprising:
   a proximal section, the proximal section having a central longitudinal axis;
   a distal section having (i) a first wing including first base struts, the first base struts extending from a first side of the distal section and (ii) a second wing including second base struts, the second base struts extending from a second side of the distal section, substantially diametrically opposing the first side, the first base struts being connected to each other by a first end strut of the first wing, the second base struts being connected to each other by a second end strut of the second wing;
   at least two junctures between the proximal section and the distal section, the first wing and the second wing being fixedly connected to each other only at the at least two junctures, wherein each of the first base struts extends from a different one of the at least two junctures and each of the second base struts extends from a different one of the at least two junctures, each of the first base struts being between the first end strut and a corresponding one of the at least two junctures, each of the second base struts being between the second end strut and a corresponding one of the at least two junctures;
   expanding the intraluminal device, such that the second wing extends transverse to the central longitudinal axis from the second side to the first side through an opening in the first wing, such that the first end strut is on the second side and the second end strut is on the first side.

12. The method of claim 11, wherein the intraluminal device is positioned in the body vessel while within a sheath, and wherein the expanding comprises withdrawing the sheath.

13. The method of claim 11, wherein the expanding comprises expanding the proximal section radially outwardly against a wall of an afferent vessel.

14. The method of claim 11, wherein the expanding comprises positioning the distal section to abut walls of efferent vessels.

15. The method of claim 11, wherein, after the expanding, the intraluminal device does not cross a central flow path from an afferent vessel to efferent vessels.

16. The method of claim 11, wherein the expanding the intraluminal device comprises expanding the distal section at an aneurysm.

17. The method of claim 16, wherein the expanding the intraluminal device comprises expanding the distal section to span an ostium of the aneurysm.

18. The method of claim 16, wherein the expanding the intraluminal device comprises expanding at least a portion of the distal section to extend within the aneurysm.

19. The method of claim 16, further comprising delivering an implant through the distal section and into the aneurysm, whereby dislodging of the implant out of the aneurysm is inhibited by the distal section.

20. The method of claim 16, wherein, after the expanding, flow into or out of the aneurysm is at least partially diverted.

* * * * *